(12) United States Patent
Su et al.

(10) Patent No.: US 7,390,639 B2
(45) Date of Patent: Jun. 24, 2008

(54) STAPHYLOCOCCAL NUCLEASE FUSION PROTEINS FOR THE PRODUCTION OF RECOMBINANT PEPTIDES

(75) Inventors: Zhengding Su, St-Laurent (CA); Feng Ni, Pierrefonds (CA)

(73) Assignee: National Research Council of Canada, Ottawa, Ontario ( * ) Notice: Subject to any disclaimer, the term of this patent is extended or adjusted under 35 U.S.C. 154(b) by 127 days.

(21) Appl. No.: 10/524,053

(22) PCT Filed: Aug. 7, 2003

(86) PCT No.: PCT/CA03/01197

§ 371 (c)(1),
(2), (4) Date: Oct. 17, 2005

(87) PCT Pub. No.: WO2004/015111

PCT Pub. Date: Feb. 19, 2004

(65) Prior Publication Data

US 2006/0173164 A1    Aug. 3, 2006

(51) Int. Cl.
*C12P 21/04* (2006.01)
(52) U.S. Cl. .............. 435/69.7; 536/23.7; 536/24.1; 435/320.1; 435/69.1; 435/252.3
(58) Field of Classification Search ........... 536/23.7, 536/24.1; 435/320.1, 69.1, 69.7, 252.3
See application file for complete search history.

(56) References Cited

U.S. PATENT DOCUMENTS 4,977,089 A * 12/1990 Kovacevic et al. ..... 435/252.31
6,365,347 B1 * 4/2002 Murray et al. ................. 435/6

OTHER PUBLICATIONS

Rudinger et al. (Jun. 1976. Peptide Hormones. Biol.Council. pp. 5-7).*
Mikayama et al. (Nov. 1993. Proc.Natl.Acad.Sci. USA, vol. 90: 10056-10060).*

* cited by examiner

*Primary Examiner*—Jennifer E. Graser
(74) *Attorney, Agent, or Firm*—Ogilvy Renault LLP

(57) ABSTRACT

Peptides are produced as fusions with a suitable carrier protein. The carrier protein disclosed herein are adapted from the N-terminal domain of *staphylococcus* nuclease. This novel carrier protein acts to promote the over-expression of the peptide-protein fusion in the form of inclusion bodies, which minimizes in-cell proteolysis of desired peptides. The fusion protein is readily purified by conventional procedures or His-tag affinity chromatography when His-tag is inserted into the fusion protein. The target peptide is released from the purified fusion protein by a simple cleavage step and separated from the librated carrier protein by use of a reverse-phase HPLC process or by repeating the same affinity purification method. A particular advantage of the disclosed method, in addition to the obvious advantage of high yields, is its use for producing isotopically labeled peptides for NMR characterization of bioactive peptides and their interactions with target proteins.

19 Claims, 16 Drawing Sheets

FIG. 1A
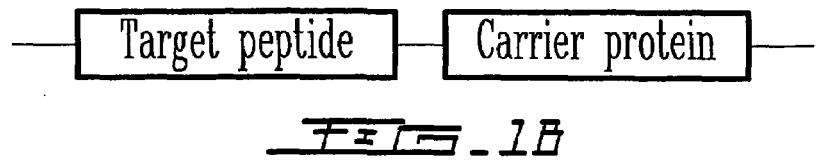
FIG. 1B
$T_1-A_1-X_1-A_2-X_2-A_3-X_3-A_4-X_4-A_5-A_6-A_7-X_5-A_8-A_9-T_2$
FIG. 2
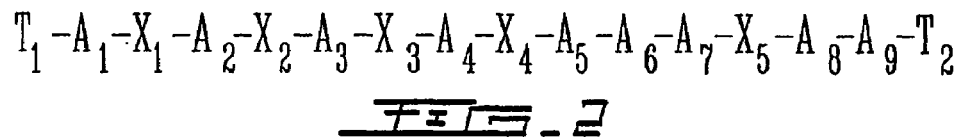
FIG. 3A
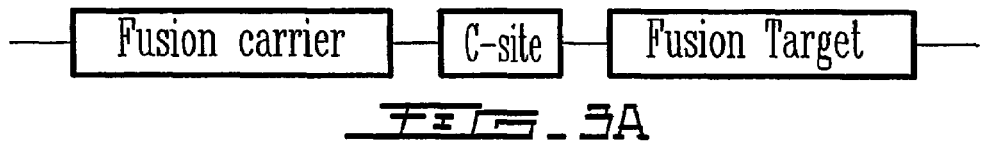
FIG. 3B
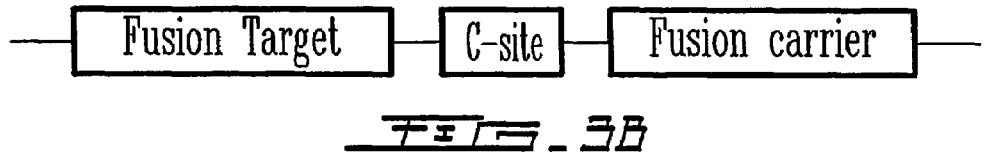
FIG. 4A
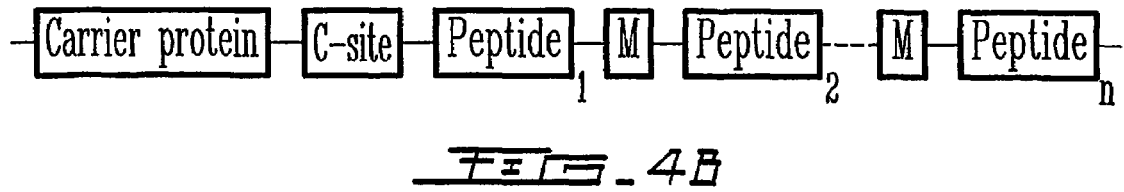
FIG. 4B

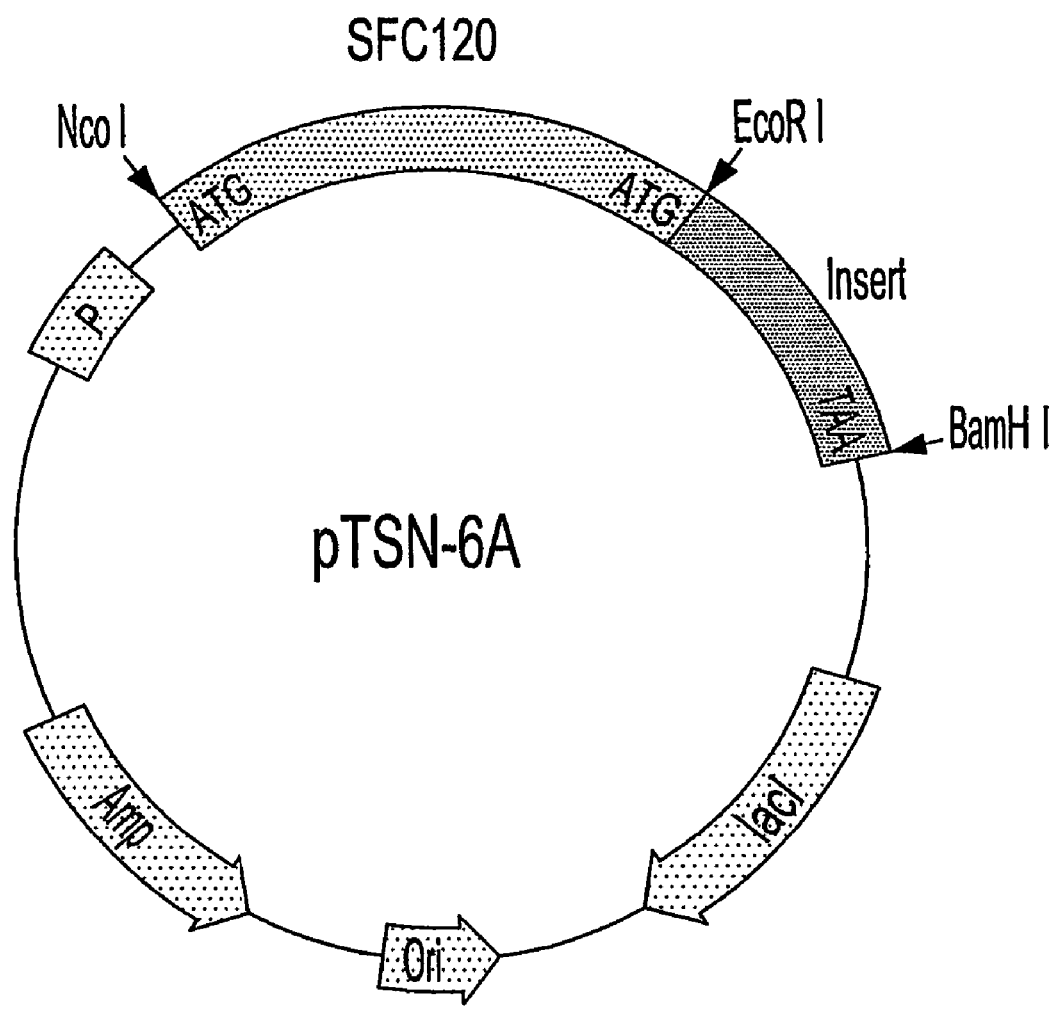
FIG_2

CRIB CONSENSUS    *ISXPXXFXHXXHVG*    SEQ ID No: 48

```
            -4    1    5    10   15   20   25   30   35   40  44
            |     |    |    |    |    |    |    |    |    |   |
CaCla4    SVLTGGNSGVSGPINETHKVHVGFDPASGNFTGLPDTWKSLLQHSKIT    SEQ ID No: 44
                           eCla4
                     mCla4              eCla4
CaSte20    EVNIKISTPFNAKHLAHVGID-DNGSYTGLPIEWERLLSASGIT       SEQ ID No: 45
                          eSte20
                     mSte20             cSte20
```

FIG_9

```
CGG AGC AGG CCC TCT TTC CAT CCC GTG TCG GAT GAG CTG GTC AAC
 R   S   R   P   S   F   H   P   V   S   D   E   L   V   N   15
TAT GTC AAC AAA CGG AAT ACC ACG TGG CAG GCC GGG CAC AAC TTC
 Y   V   N   K   R   N   T   T   W   Q   A   G   H   N   F   30
TAC AAC GTG GAC ATG AGC TAC TTG AAG AGG CTA TGT GGT ACC TTC
 Y   N   V   D   M   S   Y   L   K   R   L   C   G   T   F   45
CTG GGT GGG CCC AAG CCA CCC CAG AGA GTT ATG TTT ACC GAG GAC
 L   G   G   P   K   P   P   Q   R   V   M   F   T   E   D   60
CTG AAG    SEQ ID NO: 46
 L   K     SEQ ID NO: 47
```

FIG. 14

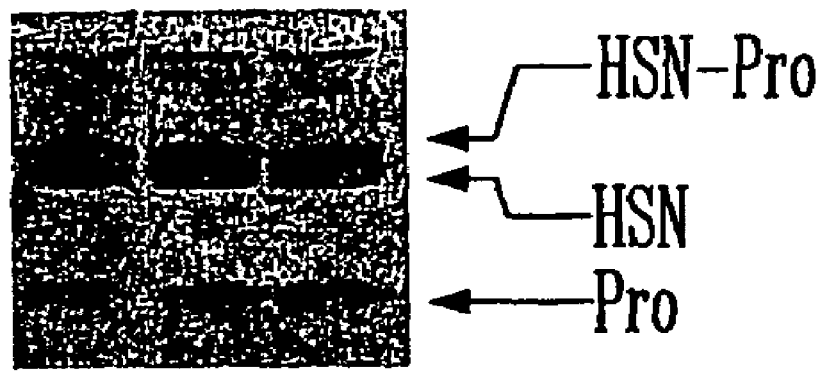
FIG._15A
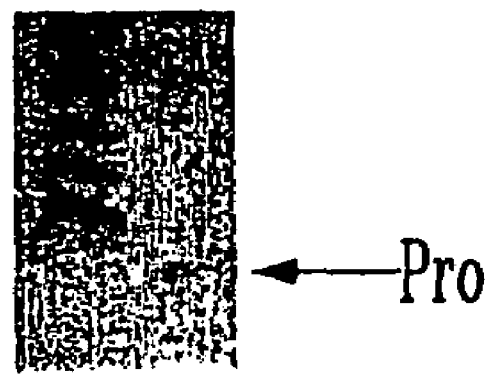
FIG._15B

FIG_18

FIG_19

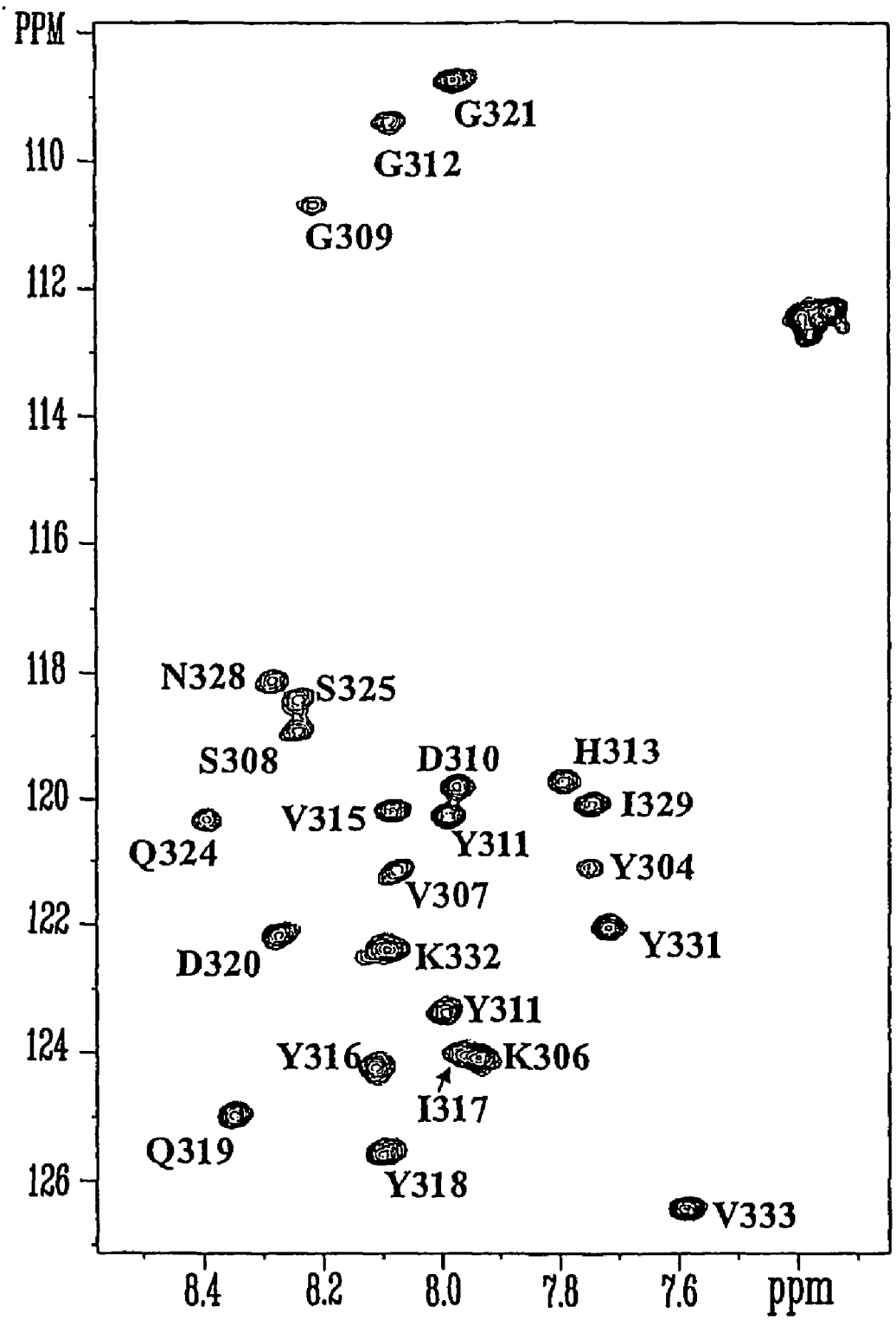
FIG_22

STAPHYLOCOCCAL NUCLEASE FUSION PROTEINS FOR THE PRODUCTION OF RECOMBINANT PEPTIDES

BACKGROUND OF THE INVENTION (a) Field of the Invention

The present invention relates generally to methods of producing recombinant peptides by using of novel carrier proteins derived from the wild-type *staphylococcus* nuclease and its mutants.

(b) Description of Prior Art

Peptides constitute a group of biomolecules for which there is an increasing demand in many fields of biological, medical and pharmaceutical research. The increasing popularity of genome-scale protein studies or proteomics is further to increase the use of peptides for functional characterization and target validation. In addition to the use of peptides as drugs (Latham, P. W., *Nature Biotech.* 17, 755-757, 1999), peptides are also tools for investigating protein-protein interactions and as lead molecules for drug design. Indeed, the bound conformations of peptides in complex with target proteins are commonly used as templates for the discovery of small-molecule drugs (Mazitschek, R. et al., *Mini. Rev. Med. Chem.,* 2; 491-506, 2002). There is also increasing evidence for the existence of peptide-like, or naturally unfolded, proteins which are encoded by the genomes and endowed with critical functional activities (Wright, P. et al., *J. Mol. Biol.,* 293; 321-331, 1999; Uversky, V., *Prot. Sci.,* 11; 739-756, 2002; Dunker, A. et al., *Biochemistry,* 41; 6573-6582, 2002).

Currently, chemical methods are used for the preparation of a variety of pharmaceutical peptides such as calcitonin, PTH, bivalirudin or other hirudin analogs and insulin. These purely chemical methods require the condensation of the corresponding amino acids or peptide fragments and very often suffer from cost disadvantages due to the use of elaborate purification methods and sometimes unnatural amino acids required. Given the increasing demand for peptides in pharmaceutical and biotechnology research, it is somewhat surprising that the main source of peptides still comes from synthetic techniques. Although solid-phase synthesis can produce good yields of peptides, the cost of synthetic peptides becomes unviable and/or prohibitively high when the desired peptide is greater than 30 residues. Moreover, uniform isotopic enrichment with $^{15}N/^{13}C$ or $^{2}H$ for NMR studies is practically impossible for larger peptide fragments by solid-phase peptide synthesis.

For many years, it has been a common practice to use fusion proteins for the expression of small peptides. The commercially available carrier proteins are GST from Pharmacia, CBD from NEB, and some others from Novagen. Most fusion carriers have been selected to increase the solubility of the fusion constructs and the fusion carriers have been so large that the final yields of the expressed peptides are very low. The large sizes of the fusion carriers also complicate the purification steps of recombinant peptides. These findings indicate that production of recombinant peptides has been problematic for many (often unknown) reasons. In particular, the large size of the fusion carrier often limits the final yield of the target peptide. Quite often, secondary cleavage sites release undesirable peptides from the fusion carrier, which complicate the purification procedure. Sometimes, the fusion protein needs to be solubilized in a suitable buffer to facilitate peptide release by use of a specific protease. This is especially the case when there is at least one cleavage site (e.g. by CNBr) within the targeted peptide. Moreover, the production of peptides for preclinical and clinical evaluations often requires multi-gram quantities (Latham, P. W., *Nature Biotech.* 17, 755-757, 1999). To achieve the latter goal, high-yield expression of the fusion protein and simplified downstream processing steps need to be developed by the engineering of new carrier proteins.

Recombinant production of peptides has many advantages over chemical (solid-phase) synthesis including potentially higher yield, lower cost, easier scale-up and less environmental contamination. Although any polypeptide chain can be theoretically expressed in any microbial system, expression of peptides can sometimes be problematic in microbial hosts, such as *Escherichia coli*. The stability of the peptide expressed often results in a diminishingly low yield. In fact peptides expressed in a host cell can be degraded quickly by endogenous proteases and assimilated by the host cell. To overcome this problem, peptides can be expressed as fusion proteins with a suitable carrier protein. The fusion protein may in addition direct the peptides to specific subcellular compartments or inclusion bodies with the goal of achieving high yield of expression and avoiding protease degradation. The most significant carrier proteins used for the expression of peptides are listed as follows.

BPI

Better reported methods to produce human a atrial natriuretic peptide (U.S. Pat. No. 5,851,802 and WO00/55322). The inventor designed a series of recombinant expression vectors that encode peptide sequences derived from bactericidal/permeability-increase protein (BPI) as carrier proteins.

Carbonic Anhydrase

Partridge et al described methods to produce recombinant peptides by use of carbonic anhydrase as the carrier protein (WO96/16297). Three peptides including GRF (1-41), GLP1 (7-34) and PTH(1-34) had been successfully prepared in this system. Wagner et al also developed a process for the recombinant preparation of a calcitonin fragment by using the same carrier protein and the use of the fragment in the preparation of full-length calcitonin and related analogs (U.S. Pat. No. 5,962,270, and WO97/29127).

α-lactalbumin

Cottingham et al invented a process to produce peptides as fusion proteins of α-lactalbumin in the milk of transgenic mammals (WO95/27782). The fusion partner acts to promote the secretion of the peptides and allows a single-step purification based on the specific affinity of α-lactalbumin to its antibodies. The peptide is released from the purified fusion protein by a simple cleavage step and purified from the liberated α-lactalbumin by repeating the same affinity purification method. This route provided a particular advantage of producing peptides that require specific post-translational modifications.

β-galactosidase

Shen used β-galactosidase as a carrier protein to express pro-insulin in inclusion bodies (Shen S., *PNAS,* 281; 4627-4631, 1984). The isolated inclusion bodies were solubilized with formic acid and cleaved with cyanogen bromide. Kempe et al used β-galactosidase as a carrier protein to express multiple repeats of the neuropeptide substance P in inclusion bodies of *E. coli* (Kempe T. et al., *Gene,* 39; 239-245, 1985). The peptide was released from the fusion protein by CNBr cleavage in a formic acid solution. Lennick et al also used this protein in a fusion system to express human α-atrial natriuretic peptide (Lennick M. et al., *Gene,* 61; 103-112, 1987). The target peptide was inserted as multiple repeats and the purified inclusion bodies were solubilized with urea followed by endoprotease cleavage. Schellenberger et al reported a process to express insoluble inclusion bodies of a fusion protein encoding a substance P peptide with β-galactosidase (Schellenberger et al., *Int. J. Peptide protein Res.*, 41; 326-332, 1993). The isolated fusion protein was treated with chymotrypsin to separate the peptide from the carrier protein.

Chloramphenicol Acetyltransferase

Dykes et al reported a method to express human α atrial natriuretic peptide as a soluble intracellular fusion protein with chloramphenicol acetyltransferase in *E. coli* (Dykes C. et al., *Eur, J. Biochem*, 174; 411-416, 1988). The fusion protein was proteolytically cleaved or chemically cleaved with 2-(2-nitrophylphenylsulphenyl)-E-methyl-3'-bromoindolenine to release the peptide.

Glutathione-S-Transferase (GST)

Ray et al used glutathione-S-transferase (GST) to carry salmon calcitonin as a soluble intracellular fusion protein. The peptide was purified after the fusion protein was cleaved with cyanogen bromide. Hancock et al fused human neutrophil peptide 1 (HNP-1) or a hybrid cecropin/mellitin (CEME) peptide with GST and expressed the fusion proteins as inclusion bodies (WO94/04688, and Ray et al., *Bio/Technology*, 11; 64, 1993). Williamson et al used the GST expression system for the rapid and economic expression of recombinant neurotensin peptide (Williamson P. et al., *Protein Exp. and Purif.*, 19; 271-275, 2000).

L-ribulokinase

Callaway et al reported a process to use L-ribulokinase as a carrier protein to express a cecropin peptide (U.S. Pat. No. 5,206,154, and Callaway et al., *Antimicrob. Agents & Chemo*, 37; 1614-1619, 1993). The fusion protein was expressed as inclusion bodies. The fusion protein was first isolated and then solubilized in formic acid prior to CNBr cleavage.

gp-55 Protein

Gramm et al used a bacteriophage T4-encoded gp-55 protein to fuse a human parathyroid hormone peptide (PTH) (Gramm H. et al., *Bio/technology*, 12;1017-1023, 1994). The fusion protein was expressed as inclusion bodies. The inclusion bodies were reacted with milder acid to hydrolyze an engineered Asp-Pro cleavage site.

Ketosteroid Isomerase

Kuliopulos et al reported the expression in insoluble *E. coli* inclusion bodies of a fusion protein encoding multiple repeats of a yeast α-mating peptide and a bacterial ketosteroid isomerase protein (Kuliopulos A. et al., *J. Am. Chem. Soc.*, 116; 4599-4607, 1994). The isolated fusion protein was solubilized with guanidine hydrochloride prior to cyanogen bromide cleavage. Majerle et al (Majerle A. et al., *J. Biomol. NMR*, 18; 145-151, 2000) have demonstrated that isotope-labeled peptides could be prepared based on the peptide expression system first described by Kuliopulos et al. It was shown that recombinant peptide production had potentially many advantages over the solid-phase method of peptide synthesis, especially for isotope-labeled peptides of ~10 residues in size.

Ubiquitin

Pilon et al described soluble intracellular expression in *E. coli* of a fusion protein encoding peptides fused to ubiquitin. The fusion protein was cleaved with a ubiquitin specific protease (UCH-L3) (Pilon A. et al., *Biotechnol. Prog.*, 13; 374-379, 1997). Kohno et al also used ubiquitin to fuse mastoparan-X, a tetrdecapeptide known to activate GTP-binding regulatory proteins (Kohno T. et al., *J. Biomol. NMR*, 12; 109-121, 1998).

Bovine Prochymosin

Hauht et al reported the expression of a fusion protein encoding an antimicorbial peptide designated P2 and bovine prochymosin as insoluble inclusion bodies in *E. coli* (Hauht et al., *Biotechnol. Bioengineer.*, 57; 55-61, 1998). The purified inclusion bodies were solubilized in formic acid and cleaved with cyanogen bromide.

GB1 Domain

Darrrinm et al used the GB1 domain as carrier protein to express the inhibitory region of Ctnl, clp (Darrrinm et al., *Biochemistry*, 41; 7267-7274, 2003). The fusion strategy takes advantage of the small size, stable fold and high bacterial expression capability of the GB1 domain to allow direct NMR spectroscopic analysis (Huth J et al, *Protein Science*, 6; 2359-2364, 1997). Pei et al used the GB1 domain as a solubility-enhancement tag (SET) for NMR studies of poorly behaving proteins (Pei et al., *J. Biomolecular NMR*, 2001).

RNA-Binding Domain

Sharon et al reported an expression system to produce the 23-residue V3 peptide, the third variable loop of the envelop glycoprotein (gp120) of the HIV virus, linked to a derivative of the RNA-binding domain of the human hnRNP C protein (Sharon M. et al., *Protein Exp. and Purif.*, 24; 374-383, 2002).

SH2 Domain

Fairlie et al reported the use of the N-terminal SH2 domain of the intracellular phosphatase, SHP2, as a carrier protein to express six peptides of ~14 residues in length. This small protein domain confers an advantage for the production of disulfide-containing peptides (Fairlie W. et al., *Protein Exp. and Purif.*, 26; 171-178, 2002).

A number of other publications have reported alternative peptide expression systems and described their utility for the production of one or two specific peptides (Baker, R., *Curr. Opin. Biotechnol.*, 7; 541-546, 1996; Campbell, A. et al., *Biochemistry*, 36; 12791-12801, 1997; Jones, D. et al., *Biochemistry*, 39, 1870-188, 2000; Lindhout, D. et al., *Biochemistry*, 41; 7267-7274, 2002; Sprules T. et al., *J. Biol. Chem.*, 278; 1053-1058, 2003). In general, the target peptides are fused to a highly expressed carrier protein in order to overcome the problem of low yields of peptide production. In some cases a carrier protein with low solubility has been exploited to direct the peptide to the inclusion bodies, thereby minimizing proteolysis and simplifying purification (Kuliopulos A. et al., *J. Am. Chem. Soc.*, 116; 4599-4607; 1994; Majerle A. et al., *J. Biomol. NMR*, 18; 145-151, 2000; and Jones, D. et al., *Biochemistry*, 39; 1870-188, 2000).

However, there is still the question of expression yields and whether the available method is suitable for the production of peptides of larger sizes. Currently available methods for peptide expression also have many technical problems especially for the production of pharmaceutical peptides of small to medium sizes (e.g. >30 residues), which are often required for reducing side effects. Practically, it is very difficult to produce peptides using a normal recombinant system such as the GST fusion expression vector. The peptides are either not expressed or degraded by proteases for unknown reasons.

It would be highly desirable to be provided with a new fusion protein overcoming the drawback of the prior art, for the production of recombinant peptides.

SUMMARY OF THE INVENTION

One aim of the present invention is to provide a novel carrier protein to construct stable expression systems for the production of recombinant peptides as fusion proteins. The fusion proteins need to be expressed in intact and stable forms. Preferably, the carrier proteins should also be easily removed by convenient methods and should not complicate subsequent steps of peptide purification. In one embodiment of the invention, the desired peptides are targeted to form inclusion bodies by engineering the carrier protein of the present invention for protection against in-cell proteolytic degradation.

In accordance with the present invention there is provided a fusion carrier protein for expressing a target peptide, said fusion carrier protein being derived from *Staphylococcus* nuclease, or a mutant thereof, and consisting of between 80 and 120 amino acid in length.

Preferably, the fusion carrier protein has an amino acid sequence as set forth in Formula I:

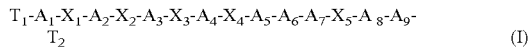

Wherein
$T_1$ is absent, a His-tag or at least one peptidic cleavage site,
$A_1$ is Ala-Thr-Ser-Thr-Lys-Lys-Leu-His-Lys-Glu-Pro-Ala-Thr-Leu-Ile-Lys-Ala-Ile-Asp-Gly-Asp-Thr-Val-Lys-Leu (SEQ ID NO:1),
$X_1$, $X_2$, $X_3$, $X_4$, and $X_5$, each independently is any one amino acid or a His-tag,
$A_2$ is Tyr-Lys-Gly-Gln-Pro (SEQ ID NO:2),
$A_3$ is Leu-Leu-Leu-Val-Asp-Thr-Pro-Glu-Thr-Lys-His-Pro-Lys-Lys-Gly-Val-Glu-Lys-Tyr-Gly-Pro-Glu-Ala-Ser-Ala-Phe-Thr-Lys-Lys (SEQ ID NO:3),
$A_4$ is Val-Glu-Asn-Ala-Lys-Lys-Ile-Glu-Val-Glu-Phe-Asp-Lys-Gly-Gln-Arg-Thr-Asp-Lys-Tyr-Gly-Arg-Gly-Leu-Ala-Tyr-Ile-Tyr-Ala-Asp -Gly-Lys (SEQ ID NO:4),
$A_5$ is Val-Asn-Glu-Ala-Leu (SEQ ID NO:5),
$A_6$ is absent or at lest one of Asp-Pro, Phe-Asn-Pro-Arg-Gly-Ser (SEQ ID NO:6) and His-tag,
$A_7$ is absent or Val-Arg-Gln-Gly-Leu-Ala-Lys-Val-Ala-Tyr-Val-Tyr-Lys-Pro (SEQ ID NO:7),
$A_8$ is absent or at least one of Asp-Pro and Phe-Asn-Pro-Arg-Gly-Ser (SEQ ID NO:6),
$A_9$ is absent or Asn-Asn-Thr-His-Glu-Gln-Leu-Leu-Arg-Lys-Ser-Glu-Ala-Gln-Ala-Lys-Lys-Glu-Lys-Leu-Asn-Ile-Trp-Ser-Glu-Asp-Asn-Ala -Asp-Ser-Gly-Gln (SEQ ID NO:8), and
$T_2$ is absent, a His-tag or at least one peptidic cleavage site.

The peptidic cleavage site can be selected for example from the group consisting of Met, Asp-Pro, Gly-Pro, Asp-Gly, Phe-Asn-Pro-Arg (SEQ ID NO:9), Leu-Val-Pro-Arg (SEQ ID NO:10), Phe-Asn-Pro-Arg-Gly-Ser (SEQ ID NO:6), and Asp-Asp-Asp-Asp-Lys (SEQ ID NO:12).

The His-tag is preferably composed of three to eight histidine residues.

In accordance with the present inventyion, there is also provided a fusion carrier protein comprising a sequence as set forth in SEQ ID NO:14, SEQ ID NO:16, SEQ ID NO:18, SEQ ID NO:20 or SEQ ID NO:24.

In one embodiment of the invention, a fusion protein comprises the fusion carrier protein as defined above, linked to at least one target peptide. The target peptide can be linked to the C- or N-terminus of the fusion carrier protein. Typically, the target peptide has a sequence between 2 and 100 amino acids in length. Of course a longer target peptide can also be used in the present invention.

In one embodiment of the invention, the target peptide is preferably selected from the group of peptide consisting of eCla4, eSte20, hirudin, mCla4, mSte20, cCla4, cSte20, FpA, FD22, propeptide of human Cathepsin B, PTH and EphrinB, or fragments thereof.

The fusion protein preferably further comprises a peptidic cleavage site between the fusion carrier protein and the target peptide.

In accordance with the present invention, there is further provided a nucleic acid sequence encoding the fusion protein described above.

Still in accordance with the present invention, there is provided an expression vector comprising the nucleic acid sequence described above, operably linked to a promoter for expression of said nucleic acid sequence coding for the fusion protein.

The promoter can be for example the pL promoter, λ promoter, trc promoter or T7 promoter.

Further in accordance with the present invention, there is provided a host cell, such as *E. coli* DH5α, BL21, JM101 or JM105 or NM522 or N99Cl+, transformed with the expression vector described above.

Preferably, the host cell is from *E. coli* or *B. subtilis*. Alternatively, the host cell can be a yeast.

In accordance with the present invention, there is provided a method for producing a fusion protein comprising the step of culturing the host cell as defined above under suitable conditions for expression of the expression vector, thereby producing a fusion protein. The suitable conditions can comprise an inducer for inducing the host cell to express the espression vector. Such inducer can be IPTG, nalidixic acid or temperature. In one embodiment of the invention, the method further comprises a step of purification of the fusion protein produced.

The step of purification preferably comprises at least one of alcohol precipitation, ion-exchange, and affinity purification using Ni-agarose resin. In such method, the fusion protein is preferably further subjected to a proteolytic digestion to release the target peptide from the fusion protein. The proteolytic digestion can be for example achieved by CNBr, formic acid or HCl or by thrombin, or a protease, such as an enterokinase. The target peptide released can be further purified by HPLC.

In accordance with the present invention, there is provided the use of either a fusion carrier protein, or a nucleic acid, both as defined above, for expressing a target peptide. The nucleic acid can be used in an expression vector for expressing the target peptide. Host cell as described above can also be used for expressing a target peptide.

For the purpose of the present invention the following terms are defined below.

The term "SFC" as used herein refers to a polypeptide derived from or based on the protein sequences of *staphylococcus* nuclease and its methionine-free and proline-free mutants (Su Z. et al., The Third Symposium on Biological Physics, American Institute of Physics, Ed by H. Franenfelder, 1998; Walkenhorst W. et al., *Biochemistry*, 36; 5795-5805, 1997; and Maki K. et al., *Biochemistry*, 38; 2213-2223, 1999) and other truncation mutants (Su Z. et al., *Biophysical J*, 76, 2; 1999). The amino acid sequence of the entire *staphylococcus* nuclease and the nucleic acid sequence of DNA encoding the protein have been reported by Shortle et al (Shortle D. et al., *Gene*, 22; 181-189, 1983), the entire content of which incorporated herein by reference.

The target peptide refers to any small protein or oligopeptide desired as a product. For practical applications of the invention, a peptide should contain at least two amino acid residues linked by peptide bonds.

The "cleavage site" as used herein refers to the amino acid sequence, which contains an amino acid or a sequence of amino acids that provides a recognition site for a chemical agent or an enzyme such that the peptide chain is cleaved at that site by the chemical agent or enzyme.

A "transformed bacterial host cell" refers to a bacterial cell that contains recombinant material or a bacterial cell that contains genetic material required for the expression of a recombinant product. The genetic material may be introduced into the cell by any known method including transformation, transduction, electroporation and infection. Generally, throughout the present application, the term "transformed" or "transformation" will be used to refer to indistinctly to any of the known method referred above.

BRIEF DESCRIPTION OF THE DRAWINGS

FIGS. 1A and 1B illustrate possible arrangement of the fusion protein of the present invention, wherein a target peptide is linked to the C-terminus (FIG. 1A) or the N-terminus (FIG. 1B) of the carrier protein;

FIG. 2 illustrates the composition of the carrier protein of the present invention;

FIGS. 3A and 3B illustrate various embodiments of the fusion protein of FIGS. 1A and 1B, wherein a cleavage site (C-site) links the carrier protein and the target peptide;

FIGS. 4A and 4B illustrate two other embodiments of the fusion protein of the present invention with single (FIG. 4A) or multiple (FIG. 4B) repeats of target peptides;

FIG. 5 illustrates pTSN-6A expression vector containing a unique protein domain, SFC120, used as the carrier protein;

FIG. 9 illustrates a summary of the CRIB peptide fragments of the *Candida* Ste20 and Cla4 proteins chosen for expression in accordance with the method of the present invention;

FIGS. 11A to 11D illustrate a SDS-PAGE of the expressed SFC-CRIB fusion proteins, wherein FIG. 11A shows expression of SFC120-mCla4, FIG. 11B shows purification of SFC120-mCla4, FIG. 11C shows expression of His-SFC120-eSte20; and FIG. 11D shows purification of His-SFC120-eSte20 from Ni-NTA agarose column;

FIG. 14 illustrates an amino acid sequence and a cDNA sequence of the propeptide of human cathepsin B;

FIGS. 15A and 15B illustrate a SDS-PAGE analysis of the cleavage of the HSN-PRO fusion protein by thrombin, wherein the fusion protein was cleaved by thrombin in FIG. 15A and of the purified PRO peptide in FIG. 15B;

FIG. 22 illustrates $^1$H-$^{15}$N HSQC spectra of the EB3 peptide with assignments.

DETAILED DESCRIPTION OF THE INVENTION

Figure 6:
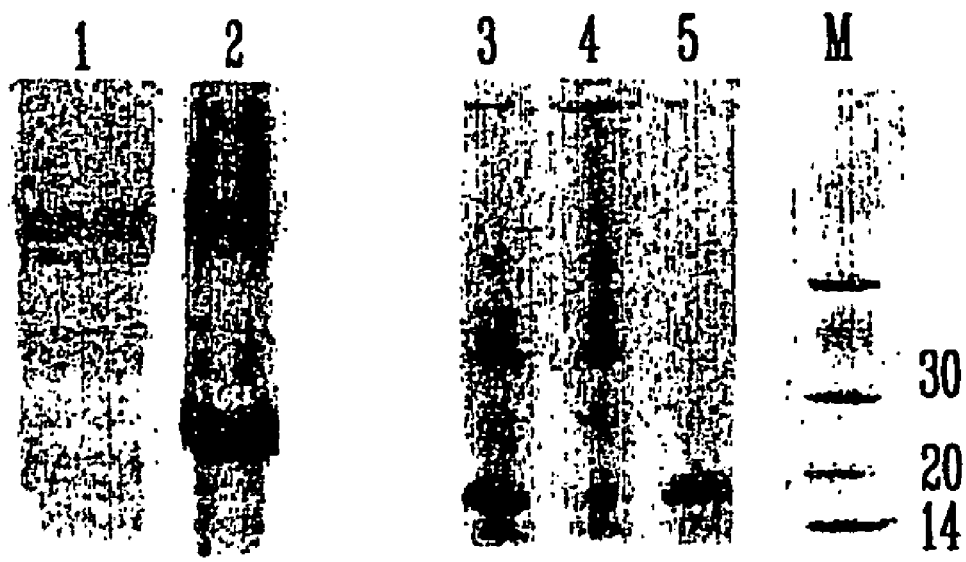
FIG. 6 illustrates a SDS-PAGE of the expressed SFC120-HRC1 fusion protein.

The expression of recombinant peptides by fusion proteins in either soluble form or in inclusion bodies is a well-known methodology. The present invention utilizes novel carrier proteins to provide an alternative approach for the production of recombinant peptides. The carrier proteins are a series of protein fragments with residues ranging from 100 to 120 amino acids designated as Small Fusion Carriers (SFCs), which are derived from the protein sequences of *staphylococcus* nuclease and its mutants. Recombinant peptides encoded by and released from fusion proteins are recovered according to these methods described herein. The invention provides fusion protein constructs to establish a new, low cost and highly efficient method for large-scale preparation of recombinant peptides.

In accordance with the present invention, there is thus provided a method for the production of recombinant peptides by use of a novel fusion protein. The carrier protein is derived from *staphylococcus* nuclease and its mutants. In this invention, a series of protein fragments ranging from 100 to 120 amino acids residues and intact proteins are engineered as carriers (termed as Small Fusion Carriers or SFCs) for the target peptides. The fusion protein led by an SFC is highly expressed in *E. coli* in the form of inclusion bodies. The SFC and the target peptide may be linked through a proteolytically-sensitive (cleavage) site. The cleavage site is typically a specific amino acid or a specific sequence of amino acids to generate fusion proteins, which are selectively cleaved by a cleavage agent. The cleavage agent can be a chemical agent such as cyanogen bromide or acid. The cleavage agent can also be an endopeptidease such as thrombin, enterokinase or another specific protease.

One embodiment of the invention provides an improved method for obtaining a recombinant peptide from bacterial cells after expression inside the cells of a fusion protein in insoluble inclusion bodies. Expression of the fusion protein as inclusion bodies increases the production yield of the recombinant peptide and protect the integrity of the target peptide.

The second embodiment of the invention is directed to an improved method to simplify purification steps by the insertion of one or more His-tag into SFCs. After cleavage of the fusion protein is achieved by a chemical reagent or by an endopeptidase, the SFC can be removed by repeating the His-tag affinity purification. Thus, the contaminations from digestion of other cellular proteins can be greatly reduced.

The third embodiment is directed to a method to express the target peptides containing methionine residues. The fusion protein is expressed in inclusion bodies and purified under a denaturing condition, e.g. with urea or guanindine hydrochloride. The fusion protein can be refolded by dialysis against a physiological buffer. The fusion protein can be then cleaved with thrombin or enterokinase to release the target peptide. After the cleavage of the fusion protein, the fragment containing SFC can be removed by chromatography or by precipitation.

The fourth embodiment of this invention covers the fusion of the target peptide to the C- or N-terminus of the carrier protein as illustrated in FIG. 1. The size of the target peptide can be from 2 to one hundred amino acid residues. The carrier protein is composed of the sixteen segments of amino acid sequences as described in FIG. 2. The amino acid sequence of each segment is listed in Table 1.

TABLE 1

The amino acid sequences of each segment of SFC

| SEQ ID NO: | Segment | Amino acid sequences |
|---|---|---|
|  | T1 | His-tag* and/or Met |
| 1 | A1 | Ala-Thr-Ser-Thr-Lys-Lys-Leu-His-Lys-Glu-Pro-Ala-Thr-Leu-Ile-Lys-Ala-Ile-Asp-Gly-Asp-Thr-Val-Lys-Leu |
|  | X1 | Any amino acid or His-tag |
| 2 | A2 | Tyr-Lys-Gly-Gln-Pro |
|  | X2 | Any amino acid or His-tag |
| 3 | A3 | Thr-Phe-Arg-Leu-Leu-Leu-Val-Asp-Thr-Pro-Glu-Thr-Lys-His-Pro-Lys-Lys-Gly-Val-Glu-Lys-Tyr-Gly-Pro-Glu-Ala-Ser-Ala-Phe-Thr-Lys-Lys |
|  | X3 | Any amino acid or His-tag |
| 4 | A4 | Val-Glu-Asp-Ala-Lys-Lys-Ile-Glu-Val-Glu-Phe-Asp-Lys-Gly-Gln-Arg-Thr-Asp-Lys-Tyr-Gly-Arg-Gly-Leu-Ala-Tyr-Ile-Tyr-Ala-Asp-Gly-Lys |
|  | X4 | Any amino acid or His-tag |
| 5 | A5 | Val-Asn-Glu-Ala-Leu |
| 6 | A6 | absent or Asp-Pro, Phe-Asn-Pro-Arg, or His-tag |
| 7 | A7 | absent or Val-Arg-Gln-Gly-Leu-Ala-Lys-Val-Ala-Tyr-Val-Tyr-Lys-Pro |
|  | X5 | Any amino acid or His-tag |
| 6 | A8 | Asp-Pro or Phe-Asn-Pro-Arg or His-tag |
| 8 | A9 | absent or Asn-Asn-Thr-His-Glu-Gln-Leu-Leu-Arg-Lys-Ser-Glu-Ala-Gln-Ala-Lys-Lys-Glu-Lys-Leu-Asn-Ile-Trp-Ser-Glu-Asp-Asn-Ala-Asp-Ser-Gly-Gln |
|  | T2 | absent or His-tag |

*His-tag described in this table is composed of three to twelve histidines.

Another embodiment of this invention provides a new expression system to produce superior or at least similar yields of purified peptides for a variety of peptide sequences of differing lengths and amino acid compositions (Table 1). In particular, the high yields of peptide production allow isotopic enrichment, including double ($^{15}N/^{13}C$)- or triple-labeling with the $^{15}N/^{13}C/^{2}H$ isotopes, of the target peptides to be used for the study of bioactive peptides and peptide-protein interactions by use of NMR spectroscopy.

Finally, the invention also provides fusion protein constructs that include an SFC and a target peptide. The target peptides include any amino acid sequence or a peptide selected from the peptide group discovered through a phage display library. Overall, in the present invention, the size of the carrier proteins (c.a. 100~200 aa) is much smaller than those used by most commercial vectors. The new expression constructs are stable in E. coli host strains and the fusion proteins are expressed in high yields. All the engineered single-chain carrier polypeptides are over-expressed in E. Coli inclusion bodies in LB or $M_9$ media. Moreover, The target peptide can be easily released from the fusion protein by site-specific proteases or by chemicals such as CNBr and/or formic acid, and separated by conventional approaches such as affinity chromatography, FPLC and HPLC.

The size of the fusion protein will vary depending on the nature and number of copies of the target peptide. The fusion protein should be large enough to avoid degradation by endogenous proteases. The fusion protein is not so large that it can not be effectively expressed by bacterial cells. Generally, the size of the fusion protein is at least 50 amino acid residues and the maximum molecular weight of the fusion protein tested can reach up to 30 kDa with high expression in bacterial cells.

The fusion protein can be arranged in two ways as illustrated in FIGS. 1A and 1B. Alternatively, the target peptide is linked either to the N-terminus or to the C-terminus of the carrier protein (SFC) via a cleavage site of a specific amino acid sequence (FIGS. 3A and 3B). In FIGS. 3A and 3B, C-site contains an amino acid or a sequence of amino acids that provides a recognition site for a chemical or enzymatic reaction such that the peptide chain is cleaved at that site by the chemical agent or the enzyme.

The composition of the carrier protein is described in FIG. 2. In FIG. 2, the fusion carrier is composed of sixteen segments of amino acid sequences. The sequence of each segment is listed in Table 1.

The target peptide can be composed of one or more consecutive sequences of two (2) to one hundred (100) or more amino acid residues. The larger peptides are in particular those derived from protein sequences that do not have uniquely-folded three-dimensional structures. The various target peptides can have several forms as shown in FIGS. 4A and 4B. In FIG. 4A, one includes a single copy of the target peptide. In FIG. 4B, a second is composed of multiple tandem repeats of a single target peptide. Each repeat may be the same or a different peptide. The repeats are linked by an "interconnecting" sequence, which may be Met, or Asp-Pro, Gly-Pro, or Phe-Asn-Pro-Arg (SEQ ID NO:9) or other suitable amino acid sequences. The interconnecting sequence is not necessarily different from the "connecting sequence" which links the carrier protein and the target peptide. The use of different connection linkers provide an advantage that two or more different cleavage agents (e.g. chemicals or enzymes) can individually release the target peptide from the fusion protein and separate the individual target peptides from each other.

Particular embodiments of the fused peptide which may appear as single or multiple-linked repeats include hirudin, calcitonin, insulin, growth hormone, growth factors, growth hormone releasing factors, corticotropin, release factor, deslorelin, desmopressin, elcatonin, glucagons, leuprolide, leuteinizing hormone-releasing hormone, secretin, somatostatin, thyrotropin-releasing hormone, triptorelin, vasoactive interstinal peptide, interferons, parathyroid hormone, BH3 peptides, β-amyloidosis peptide. One common property of these peptides is that they all have flexible and fragile conformations that make them unstable and prone to proteolytic degradation.

The cleavage site and the target peptide are preferably selected so that the target peptide does not contain the same cleavage site. The cleavage sites include aspartic acid-proline (Asp-Pro), aspartic acid-glycine (Asp-Gly), methionine (Met), phenylalanine-asparagine-proline-arginine (Phe-Asn-Pro-Arg; SEQ ID NO:9), leucine-valine-proline-arginine (Leu-Val-Pro-Arg; SEQ ID NO:10), aspartic acid-aspartic acid-aspartic acid-aspartic acid-lysine (Asp-Asp-Asp-Asp-Lys. SEQ ID NO:12) or other specific amino acid sequences. New cleavage sites may be designed in order to use a chemical cleavage reagent or an enzyme or the combination of the two. In some instances, it may be desirable to utilize a cleavage site to introduce a specific functional group to the C-terminal of the target peptide such as cleavage by cyanogen bromide.

The DNA sequence encoding the target peptide may be obtained from natural sources (e.g. genomic DNA) or via chemical synthesis utilizing the codon preference of bacterial cells or other host cells.

One embodiment of the invention provides a method to amplify the DNA sequence encoding a particular peptide contained in genomic DNA. Typically, two primers are designed to introduce two unique restriction sites at each end of the PCR product. The PCR reaction is performed in a PCR amplification device which provides control of the reaction temperature. A PCR DNA polymerase, e.g. the Taq or Pfu DNA polymerase, is used in a PCR reaction and the reaction condition follows the protocol provided by the suppliers. PCR products are subjected to the direct digestion with at least one restriction enzyme or if necessary a clean-up procedure is conducted prior to restriction enzyme digestion. The digestion reaction mixture is cleaned up by DNA purification methods. DNA purification can be achieved by use of agarose gel electrophoresis or a PCR purification kit. The purified PCR products are used as inserts encoding target peptides. In some instances, the insert encoding the target peptide is not available from a natural source. In this latter case, the DNA fragment encoding the target peptide is prepared through chemical synthesis. Generally, at least two oligonucleotide primers are chemically synthesized with at least one restriction enzyme site at either end. The two oligonucleotides may be complementary or overlapped in the middle region with at least 10 base pairs. The PCR amplification may be employed to generate an intact insert from overlapped oligonucleotides.

The DNA sequence encoding a fusion protein contains at least four parts including a DNA sequence of the affinity tag, a DNA sequence of the carrier protein (e.g. SFC), a DNA sequence of the cleavage site and a DNA sequence of the target peptide. Typically, the arrangement of DNA sequence segments can be the same as those described in FIGS. 3A and 3B. The DNA sequence of the affinity tag may be inserted in any place in the DNA sequence of the fusion protein. The DNA sequence of the fusion protein is ligated into any bacterial expressible plasmid to construct an expression vector. The expression vector contains at least one promoter e.g. lac, T7, Tac, λ or pL and one antibiotic marker, e.g. ampicillin, kanamycine, or tetracycline.

The constructed expression vector may be transformed into a bacterial host cell to replicate plasmid for small-scale DNA preparation (mini-prep) and sequencing. The identity of the construct is confirmed by DNA sequencing and the expression vector is transformed into a bacterial host cell to express the fusion protein. The cells harboring the fusion protein expression vector may be cultured in the LB medium or a minimum medium in the presence of at least one antibiotic. The expression of the fusion protein is induced with an inducer, e.g. IPTG, galactoside, nalidixic acid or temperature.

The purification of fusion protein refers to the procedure by which the fusion protein is isolated from host cells. Cells are typically collected by centrifugation or filtration. The cell pellet is typically resuspended in the lysis buffer which contains 50 mM phosphate, 10 mM Tris, 50 mM NaCl. The lysis buffer may contain a chaotropic agent, e.g. urea or guanidine hydrochloride. Suspended cells may be further subjected to French Press or ultra-sonication to thoroughly break the cells. The lysate is subjected to centrifugation to isolate the desired fusion protein from others. In some instances, the fusion protein is isolated from cells as pure inclusion bodies. The inclusion bodies may be isolated from a crude cell lysate by conventional techniques, e.g. by centrifugation. The crude inclusion bodies may be subjected to an initial purification step such as washing by a solution of 50 mM phosphate, 1 mM EDTA, pH7.5 once and then washing with the same buffer containing low concentration of chaotropic reagents (such as urea or guanidine hydrochloride) at least twice. Pure inclusion bodies will be dissolved in a chaotropic buffer and then is subjected to refolding. The refolding process may be carried out by dialysis of the suspended sample against a physiological buffer or by removal of salts through a reverse-phase chromatographic column and followed by freeze-drying. In some instances, the fusion protein is produced in insoluble inclusion bodies inside cells but no affinity tag was engineered. In this case, the fusion protein in the lysate is roughly purified by solvent extraction and further purified by ion-exchange chromatography. If necessary, the fusion protein may be purified by reverse-phase HPLC. In other instances, the fusion protein may be purified through affinity chromatography such as His-tag affinity beads under either native condition or denaturing conditions.

A cleavage reaction is used to release the target peptide from the fusion protein. The reaction is carried out in a solution suitable for the activities of the chemical reagent or the enzyme. In some instances, the fusion protein is dissolved in high concentration of TFA or formic acid. If necessary, CNBr is added to a final molar ratio of 100:1. The solution is allowed to stand for 4~24 hours at room temperature in dark under $N_2$ gas. In other instances, the fusion protein is dissolved in a buffer suitable for enzymatic reaction. The suitable buffer should be selected for optimal activity of the enzyme, e.g. thrombin or enterokinase.

After cleavage, the mixture is used to isolate the target peptide from the carrier (and fusion) protein. In some instances, the mixture may be used directly for HPLC purification. The pH value of the mixture should be adjusted to below 3.0 and the sample is filtered to remove particles prior to HPLC purification. In some instances, the mixture is diluted with water (e.g. to ~10-fold) and lyophilized to dryness and then purified by reverse-phase HPLC column using an acetonitrile-water gradient containing 0.1% TFA. In other instances, the mixture is initially purified by His-tag affinity chromatography and reverse-phase chromatography to remove salts, the carrier protein, undigested fusion protein and non-specifically digested peptides. Finally, the pure peptide is lyophilized and the identity is confirmed by mass spectrometry.

Table 2 lists some recombinant peptides exemplified hereinbelow, which have been expressed with the current invention. The data show that the present expression systems can efficiently produce pure peptides in high-yield in either non-labeled or isotopically labeled form.

TABLE 2

Examples of the expressed recombinant peptides

| Peptide | Size (AA) | Yield (mg/L) | Purity | Isotope form | Medium |
|---|---|---|---|---|---|
| eCla4 (CRIB) | 48 | >15 mg | HPLC (>98%) | $^{15}$N | $M_9$ |
| eCla4 (CRIB) | 48 | ~10 mg | HPLC (>98%) | $^{15}$N/$^{13}$C/$^{2}$H | $M_9$ |
| 10 hirudin fragments | 13/ea | 10~20 mg | HPLC (>98%) | $^{15}$N | $M_9$ |
| mCla4 (CRIB) | 22 | >15 mg | HPLC (>98%) | $^{15}$N | $M_9$ |
| mSte20 (CRIB) | 22 | >15 mg | HPLC (>98%) | $^{15}$N | $M_9$ |
| cCla4 (CRIB) | 22 | >10 mg | HPLC (>98%) | $^{15}$N | $M_9$ |
| cSte20 (CRIB) | 22 | >10 mg | HPLC (>98%) | $^{15}$N | $M_9$ |
| 10 FpA fragments | 12/ea | 10~20 mg | HPLC (>98%) | $^{15}$N | $M_9$ |
| FN22 peptide | 22 | >20 mg | HPLC (>98%) | non-labeled | LB |
| FD22 peptide | 22 | >20 mg | HPLC (>98%) | non-labeled | LB |
| Hirudin$^{47-65}$ | 18 | >20 mg | HPLC (>98%) | non-labeled | LB |
| 6 tetra-peptides | 5 | >10 mg | HPLC (>98%) | $^{15}$N | $M_9$ |
| Propeptide of human Cathepsin B | 64 | 10 mg | HPLC (>98%) | $^{15}$N | $M_9$ |
| PTH | 33 | 10 mg | HPLC (>98%) | $^{15}$N | $M_9$ |
| EphrinB peptides | 33 | >15 mg | HPLC (>98%) | $^{15}$N | $M_9$ |

The present invention will be more readily understood by referring to the following examples which are given to illustrate the invention rather than to limit its scope.

EXAMPLE 1

Construction of Expression Vector pTSN1

A bacterial expression vector that encodes a fusion protein was constructed. The vector contains a sequence for a gene encoding the N-terminal nucleotide binding domain of *staphylococcus* nuclease, designated SFC120 (SEQ ID NO:14) and used as the carrier protein, linked to a sequence encoding a cleavage site and a sequence encoding a target peptide. The vector construct, pTSN1, was prepared in several steps as described below.

First, the nuclease gene was amplified from the *staphylococcus aureus* genome. A 500 base-pairs Nco I/BamH I fragment was produced by PCR reaction with two primers. Primer 1 (Nco) was used to create one Nco I site at the beginning of the gene, which has one ATG start codon. Primer 2 (BamH) was used to create one BamH I site just after the stop codon (TAA or TGA or TAG). Following the PCR reaction, the reaction mixture was immediately digested with Nco I and BamH I restriction enzymes. The new fragment was in turn ligated into the Nco I-BamH I restricted pTK vector, which was modified from one commercial plasmid of pTrc99A (Pharmacia Biotechnology, Amann, E. et al., *Gene*, 69; 301-15, 1988). The ligation products were transformed into *E. coli* JM105. The plasmid with the nuclease gene was confirmed by DNA sequencing. A clone with high nuclease expression and activity was selected and the plasmid that it harboured was named pSN.

Second, an EcoR I restriction site was generated at position 362 of the nuclease gene (SEQ ID NO:15) by sited-directed mutagenesis. The corresponding mutation produced changes of two amino acids, i.e. N118E and N119F. Site-directed mutagenesis was carried out in a Perkin-Elmer Thermocycler™ essentially by the PCR method with some modification from the protocol of QuikChange™ Site-Directed Mutagenesis Kit. The basic procedure utilizes a supercoiled, double-stranded DNA (dsDNA) vector with the insert of interest and with two synthetic oligonucleotide primers containing the desired mutation. The Pfu DNA polymerase replicates both plasmid strands with high fidelity and without displacing the mutant oligonucleotide primers. The oligonucleotide primers, each complementary to opposite strands of the vector, extend during temperature cycling by means of Pfu DNA polymerase. On incorporation of the oligonucleotide primers, a mutated plasmid containing staggered nicks is generated. Following temperature cycling, the product is treated with Dpn I to select for mutation-containing synthesized DNA. The nicked vector DNA incorporating the desired mutations is then transformed into *E. coli* JM105 competent cells.

The resultant plasmid was termed pTSN1. A gene of a target peptide with an appropriate cleavage site (e.g. Met, Asp-Pro, Gly-Pro, or Phe-Asn-Pro-Arg) and a stop codon can be inserted into pTSN1 between the EcoR I and BamH I sites. The carrier protein in this fusion construct was defined as SFC120.

EXAMPLE 2

Construction of Expression Vector pTSN-6A

In order to control the expression of the fusion protein tightly, the SFC gene of pTSN1 was moved into an expression vector (such as pET vectors) with T4 bacteriophage T7 promoter. The DNA sequence of SFC120 was amplified by standard PCR methods while the restriction enzyme site of Nco I was generated in the 5'-end and the two restriction sites of EcoR I and BamH I were generated in the 3'-end. The PCR product was double-digested with Nco I and BamH I, and ligated into the pET15M vector, which was modified from the pET-15b vector (Novagen) by removing the EcoR I site. The constructed fusion vector was defined as pTSN-6A (FIG. 5). In FIG. 5, P denotes the promoter, either T7 or Trc. His-tag with six histidines can be placed at either N-terminal or C-terminal side of the SFC120 carrier protein to simplify the purification step.

EXAMPLE 3

Construction of Expression Vector pHSN-M65L

Residue Met65 of SFC120 encoded in plasmid pTSN-6A was mutated into Leu by sited-directed mutagenesis. Site-directed mutagenesis was carried out in a Perkin-Elmer Thermocycler™ essentially by the PCR method with some modification from the protocol of QuikChange™ Site-Directed Mutagenesis Kit. The basic procedure utilizes a supercoiled, double-stranded DNA (dsDNA) vector with an insert of interest and two synthetic oligonucleotide primers containing the desired mutation. The Pfu DNA polymerase replicates both plasmid strands with high fidelity and without displacing the mutant oligonucleotide primers. The oligonucleotide primers, each complementary to opposite strands of the vector, extend during temperature cycling by the Pfu DNA polymerase. On incorporation of the oligonucleotide primers, a mutated plasmid containing staggered nicks is generated.

Following temperature cycling, the product is treated with Dpn I to select for mutation-containing synthesized DNA. The nicked vector DNA incorporating the desired mutations is then transformed into *E. coli* DH5α competent cells.

Alternatively, a sequence encoding six consecutive histidine residues was attached at the 5'-end of the DNA sequence of SFC120. The resultant plasmid was termed pHSN-M65L. The gene of the target peptide with an appropriate cleavage site (e.g. Met, Asp-Pro, Gly-Pro or Phe-Asn-Pro-Arg) and a stop codon can be inserted into pHSN-M65L between the EcoR I and BamH I sites. The fusion carrier in this fusion protein was defined as HSFC120-M65L (SEQ ID NO:18).

EXAMPLE 4

Construction of Expression Vector pMFH

Four methionine residues of SFC120 included in plasmid pTSN1 were mutated into Leu by multiple sited-directed mutagenesis. The resultant mutation produces amino acid changes at four residues, i.e. M16L, M32L, M65L and M98L. Site-directed mutagenesis was carried out in one Perkin-Elmer Thermocycler™ in three repeat steps essentially by the PCR method with some modification from the protocol of QuikChange™ Site-Directed Mutagenesis Kit.

Initially, the pTSN1 plasmid DNA was used as a template. The product from a previous PCR reaction was used as a template in the next PCR reaction. The site-directed mutagenesis reaction was repeated until all the four methionines were changed into leucine. The basic procedure utilizes a supercoiled, double-stranded DNA (dsDNA) vector with an insert of interest and two synthetic oligonucleotide primers containing the desired mutation. The Pfu DNA polymerase replicates both plasmid strands with high fidelity and without displacing the mutant oligonucleotide primers. The oligonucleotide primers, each complementary to opposite strands of the vector, extend during temperature cycling by means of Pfu DNA polymerase. On incorporation of the oligonucleotide primers, a mutated plasmid containing staggered nicks is generated. Following temperature cycling, the product is treated with Dpn I to select for mutation-containing synthesized DNA. The nicked vector DNA incorporating the desired mutations is then transformed into *E. coli* DH5α competent cells. The resultant plasmid was called as pMF (SEQ ID NO:19) and the carrier protein was designated MF (SEQ ID NO:20).

A DNA sequence encoding six-consecutive histidine residues and a multiple cloning site (MCS) was inserted at the 3'-end of the DNA sequence of MF in pMF (see, Example 1) between the EcoR I and BamH I sites. The sequence is composed of six parts as follows:

Mfe I site→six histidine→Met→EcoR I site→MCS→BamH I site.

Two complementary oligonucleotides were synthesized that encode the above sequence.

Ten (10) μg of each oligonucleotide were annealed in a 50 μl reaction solution in 10 mM Tris, 100 mM NaCl, 1 mM EDTA, pH7.8 for 5 minutes in boiling water. The sample was then slowly cooled to room temperature. One (1) μl of 100 mM ATP stock and 1 μl of T7 polynucleotide kinase were added into the reaction and the mixture was allowed to stand at 37° C. for 30 minutes and followed by purification with the Qiagen Nucleotide Remove Kit. The purification column was eluted with 50 μl of EB buffer provided by the supplier.

Ten (10) μl of the above insert was mixed with 150 ng of the pMF vector which was treated with appropriate restriction enzymes in a ligation reaction containing 50 mM Tris, 10 mM MgCl$_2$, 1 mM ATP, 1 mM DTT, pH7.5, 4 units T4 DNA ligase for 12 hours at 16° C. The resultant plasmid was termed pMFH.

The gene of the target peptide with an appropriate cleavage site (e.g. Met, Asp-Pro, Gly-Pro or Phe-Asn-Pro-Arg) and a stop codon can be inserted into pMFH between the EcoR I and BamH I sites. The carrier protein in this fusion construct was defined as MFH (SEQ ID NO:24).

EXAMPLE 5

Construction of Expression Vector pHSN

The expression construct consists of the hexahistidine-tagged SFC protein coupled to a short linker housing a thrombin cleavage and unique BamH I and EcoR I sites for in-frame insertion of peptide sequences. The target peptide sequence may be obtained from any available source, as a cDNA, a synthetic gene or a microbial genome.

To prepare the construct, the SFC sequence in pSN was initially amplified with PCR by use of the Pfu DNA polymerase (Stratagene). The oligonucleotide primers used for the PCR were 5'-cat gcc atg ggt ttc cac cat cac cat cac cat gca act tca act aaa-3' (forward, SEQ ID NO:25) and 5'-gga agatct tta gaattc cgc ggatcc acg cgg cft aaa ttg acc tga atc agc-3' (reverse, SEQ ID NO:26). The forward primer introduced one Nco I site (underlined) required for the addition of an in-frame hexahistidine tag during subcloning into a modified pET15b vector (Novagen) in a subsequent step. The reverse primer (a) introduced a new thrombin cleavage site (Phe-Asn-Pro-Arg) to the 3'-end of SFC, (b) removed the stop codon following SFC, and (c) introduced unique BamH I, EcoR I and Bgl II restriction sites (underlined). The BamH I and EcoR I sites enable direct subcloning of a BamH I/EcoR I fragment containing the target peptide sequence of interest.

Following PCR amplification, the product named as HSN insert was digested with Nco I and Bgl II enzymes and subcloned into pET15M (see Example 2), which was modified from pET15b and pET32a to remove the thioredoxin carrier. The expression plasmid was designated pHSN.

EXAMPLE 6

Expression of Hirudin Peptide HRC1

The HRC1 peptide is derived from the C-terminal 11 amino acid residues of hirudin. The HRC1 peptide has a strong inhibition of thrombin with ~1 μM of $K_i$, and the amino acid sequence is Asp-Phe-Glu-Glu-Ile-Pro-Glu-Glu-Tyr-Leu-Gln (SEQ ID NO:27). The DNA sequence encoding the HRC1 peptide was prepared by two synthetic complementary oligonucleotides with two unique restriction enzyme sites of EcoR I and BamH I at each end, respectively. The two oligonucleotide primers are 5'-aattcatggg tgacttcgaa gaaatcccgg aagaatacct gcagtaag-3' (SEQ ID NO:28) and: 5'-gatccttact gcaggtattc ttccgggatt tcttcgaagt cacccatg-3' (SEQ ID NO:29).

Two oligonucleotides were annealed in the annealing buffer (10 mM Tris, pH 7.5-8.0, 50 mM NaCl, 1 mM EDTA). The insert has flank sequences at both ends and the insert was treated with polynuleotide kinase and purified with Qiagen Nucleotide Remove Kit prior to subcloning to the vector pTSN1 (see Example 1). The ligation was conducted using a standard procedure. The construct was confirmed by DNA-sequencing and the resultant plasmid was designated pTSN1-HRC1.

Expression of the HRC1 peptide was achieved by transformation of the plasmid, pTSN1-HRC1, into the *E coli* BL21

(DE3) competent cells. As shown in SEQ ID NO:28 and SEQ ID NO:29, a single methionine residue was inserted between the SFC120 fusion carrier protein and the HRC1 peptide to facilitate the release of the peptide from the fusion protein by CNBr cleavage.

An overnight culture grown in 2YT containing 100 µg/ml ampicillin (50 ml) was used to inoculate 1 L of LB medium supplemented with 100 µg/ml ampicillin. $^{15}$N-labeled HRC1 peptide was expressed using $^{15}$(NH$_4$)$_2$SO$_4$ (1 g/L) as the sole nitrogen source in M9 medium supplemented with 100 µg/ml ampicillin. The cells were grown at 37° C. to a cell density of ~0.8 OD$_{600}$ and induced by adding IPTG to a final concentration of 1 mM. The cells were further incubated for 4-12 hours at 37° C. and collected by centrifugation (8000 rpm for 20 min). The cell pellet was frozen at −20° C. for future use.

Thawed cell pellets were resuspended in 6 M urea in 20 mM Tris, 100 mM NaCl buffer, pH 8.0 for 4 hours and then sonicated for 45 s on ice. The solution was then centrifuged at 7,000 rpm for 20 min. An equivolume of 100% cold ethanol (−20° C.) was added to the supernatant and the solution allowed to stand at 4° C. for at least 2 hours. After centrifugation, the pellet containing precipitated DNA and large proteins was discarded and another equivolume of cold ethanol was added to the collected supernatant and allowed to stand overnight. The solution was centrifuged at 8,500 rpm and the pellet containing the relatively pure fusion-peptide fragment subjected to SDS-PAGE analysis (FIG. 6). If necessary, the pellet was resuspended in 6 M urea in 10% acetonitrile, 90% H$_2$O, 0.1% TFA, pH<3.0 and applied to a Sep-Pak™ column (Waters) to remove any impurities. The fusion protein was then lyophilized. In FIG. 6, lane 1 was loaded with total protein content for uninduced cells. Lane 2 was loaded with total protein content for IPTG-induced cells. Lane 3 was loaded with the supernatant of the cell lysate with 50 mM phosphate buffer, pH8.0, 50 mM NaCl, 6M urea. Lane 4 was loaded with pellet of the first alcohol precipitation. Lane 5 was loaded with pellet of the second alcohol precipitation. Finally, lane M was loaded with molecular weight markers.

EXAMPLE 7

Expression of Tetrapeptide Substrates of Thrombin

Dynamic and relaxation dispersion NMR spectroscopy can be used to quantitate transient ligand binding to target proteins (PCT Application PCT/CA03/00014). This method is particularly useful during the early stages of the drug discovery process when weak-binding ligands are identified. This new methodology can also be applied to a mixture of peptide ligands binding either to distinct sites or competing for one site on a target protein. To facilitate experimental measurements, it is essential to prepare isotopically-labeled samples, e.g. $^{15}$N-labeled peptides.

In nature, there exist many short peptide substrates for the thrombin active site. For example, Leu-Asp-Pro-Arg (SEQ ID NO:30), Val-Asp-Pro-Arg (SEQ ID NO:31), Phe-Asn-Pro-Arg (SEQ ID NO:32), Pro-Asn-Pro-Arg (SEQ ID NO:33), Phe-Ser-Ala-Arg (SEQ ID NO:34) and Val-Ser-Pro-Arg (SEQ ID NO:35) are native tetrapeptide sequences found in proteins cleaved specifically by thrombin. These peptides can be used as models to design thrombin specific inhibitors blocking the active site.

In order to ensure approximately equal-molar concentrations of each peptide in the mixture, six peptides were incorporated into one target sequence for recombinant expression. The tetrapeptides were linked with one methionine residue. In the N-terminus of each tetrapeptide, one glycine residue was attached so that the first amide proton NMR signal of each tetrapeptide can be observed. The corresponding target peptide is composed of 35 amino acid residues (Met-Gly-Leu-Asp-Pro-Arg-Met-Gly-Val-Asp-Pro-Arg-Met-Gly-Phe-Asn-Pro-Arg-Met-Gly-Pro-Asn-Pro-Arg-Met-Gly-Phe-Ser-Ala-Arg-Met-Gly-Val-Ser-Pro-Arg; SEQ ID NO:36).

The DNA sequence encoding the target peptide was amplified by two synthetic oligonucleotides (SEQ ID NO:37, and SEQ ID NO:38) with two unique restriction enzyme sites of EcoR I and BamH I at each end, respectively. Two oligonucleotide primers are overlapped with 18 base pairs. The PCR reaction was performed with a standard PCR procedure in one Perkin-Elmer PCR amplifier. The PCR fragment was digested with EcoR I and BamH I, and purified with Qiagen PCR purification Kit. The insert was subcloned to vectors pTSN-6A (see Example 2) or pMFH (see Example 4). The expression construct was transformed into the E. coli DH5α strain and the plasmid was purified with the Qiagen mini-prep kit. The identity of the insert was confirmed by DNA sequencing. As shown in SEQ ID NO:37, a single methionine residue was also inserted between SFC or MFH and the target peptide sequence to facilitate release of the peptides by CNBr cleavage.

Figure 7:
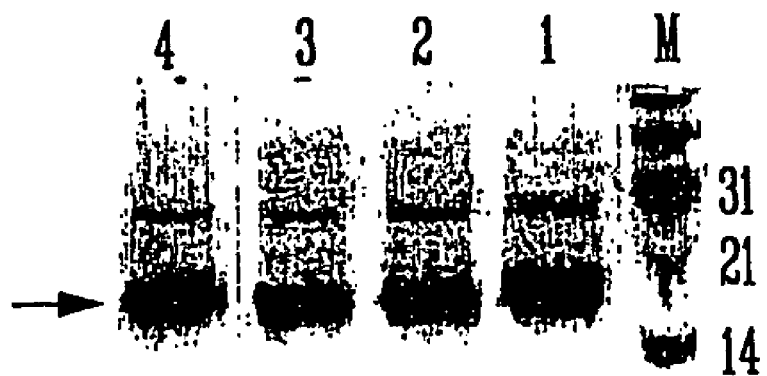
FIG. 7 illustrates a 20% SDS-PAGE analysis of the expressed fusion protein containing tetrapeptides.

Expression of the fusion protein was achieved by transformation of the plasmid into E. coli BL21 (DE3) competent cells. An overnight culture grown in 2YT containing 100 µg/ml ampicillin (50 ml) was used to inoculate 1 L of LB medium supplemented with 100 µg/ml ampicillin. $^{15}$N-labeled peptides were expressed using $^{15}$(NH$_4$)$_2$SO$_4$ (1 g/L) as the sole nitrogen source in M9 medium. The cells were grown at 37° C. to a cell density of OD$_{600}$=0.8 and induced by adding IPTG to a final concentration of 2 mM. The cells were incubated for 12 h at 37° C. and collected by centrifugation (8000 rpm for 20 min). The expression of the fusion protein was subjected to SDS-PAGE analysis (FIG. 7). The cell pellet was frozen at −20° C. for future use. In FIG. 7, lane M was loaded with molecular weight markers. Lanes 1 to 4 were loaded with the cell lysate. The expressed fusion protein in each lane is indicated by the arrow. Thawed cell pellets were resuspended in 6 M urea in 20 mM Tris, 100 mM NaCl buffer, pH 8.0 for 2 hours and then sonicated for one minute on ice. The solution was then centrifuged at 7,000 rpm for 20 min. The supernatant was subjected to the purification by Ni-NTA affinity chromatography under a denaturing condition (see the purification part in Example 8). The eluate containing the fusion protein was applied to a Sep-Pak™ column (Waters) to remove salts. The purified fusion protein was then lyophilized.

CNBr cleavage was used to release the target peptide from the fusion protein and to separate the tetrapeptides from each other. The fusion protein was dissolved in 70% TFA and CNBr added to a final molar ratio of 100:1 and the solution allowed to stand for ~24 hours. The samples were then diluted with water (×10) and lyophilized to dryness and purified by RP-HPLC on a C18™ column using an acetonitrile-water gradient containing 0.1% TFA. The peptide mixture were lyophilized and confirmed by electrospray mass spectrometry.

The data on the yields of the fusion proteins and the peptides exemplified herein are listed in Table 2.

Figure 8:
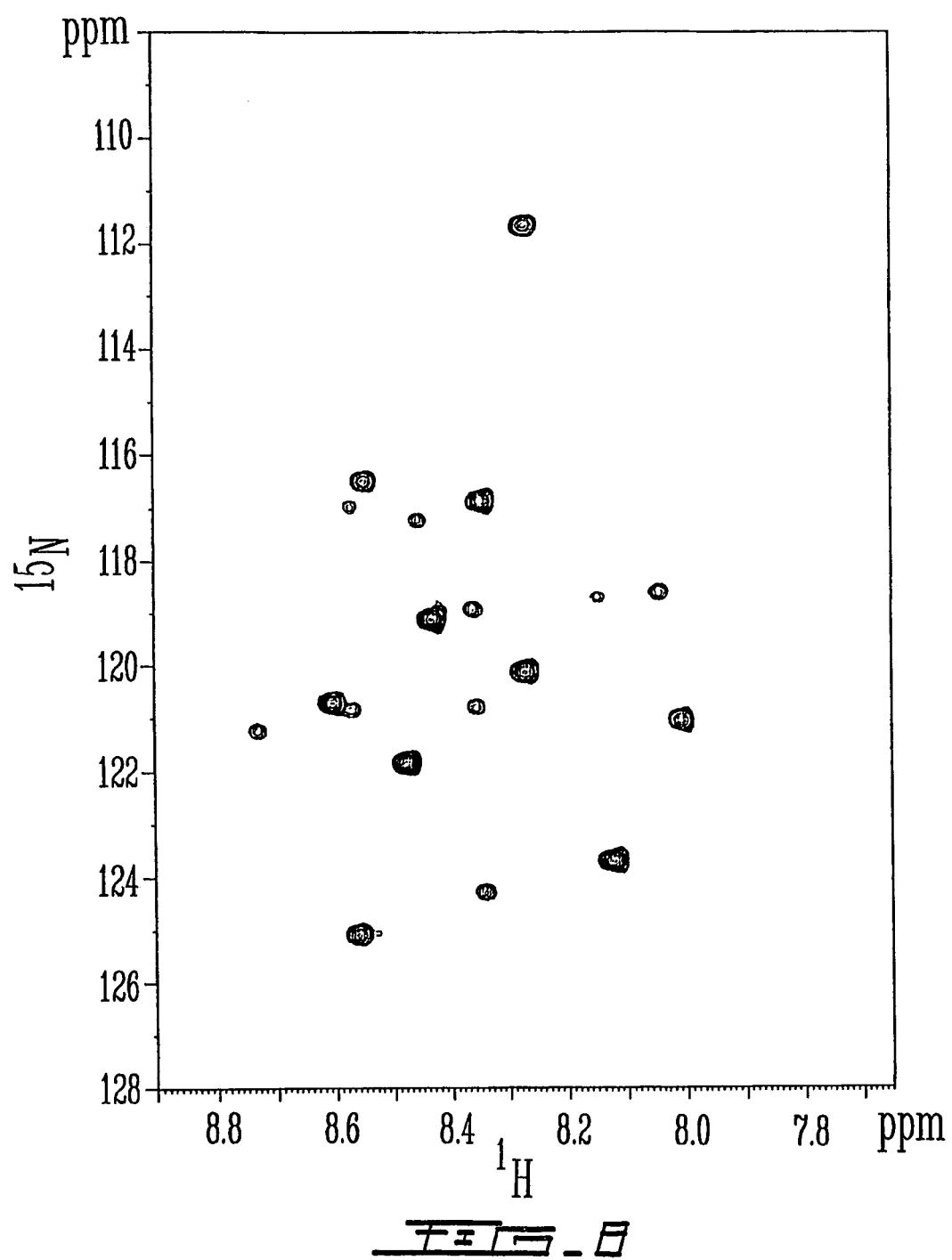
FIG. 8 illustrates $^1$H-$^{15}$N HSQC spectra of a mixture of six uniformly $^{15}$N-labelled peptides, i.e. GLDPRS$_H$, GVDPRS$_H$, GFNPRS$_H$, GPNPRS$_H$, GFSARS$_H$ and GVSPR, wherein S$_H$ is homo-serine.

$^1$H-$^{15}$N heteronuclear single-quantum correlation (HSQC) spectra were acquired at 500 or 800 MHz using a standard pulse sequence (Mori, S. et al., *J. Magn. Reson. B*, 108; 94-98, 1995). Spectral processing, display and analysis were performed using the XwinNMR software package supplied with the spectrometer system. Sequence specific assignment of peptide HSQC spectra was carried out with NMRview 4.0 (Johnson, B. et al., *J. Biomol. NMR.*, 4; 603-614, 1994). The $^{1}$H-$^{15}$N HSQC spectrum of the peptide mixture is shown in FIG. 8.

EXAMPLE 8

Expression of Isotopically Enriched CRIB Fragments

FIG. 9 summarizes the fragments of the *Candida* Ste20 and *Candida* Cla4 proteins chosen for expression based on interactions with Cdc42 reported for highly homologous kinase-Cdc42 interactions in humans (Thompson G. et al., *Biochemistry*, 37; 7885-7891, 1998; Zhang B. et al., *J. Biol. Chem.*, 272; 21999-22007, 1997; Zhao Z. et al., *Mol. Cell Biol.*, 18; 2153-2163, 1998; and Stevens W. et al., *Biochemistry*, 38; 5968-5975, 1999). The peptide sequences termed as the extended-CRIB fragments (eCla4 and eSte20, FIG. 9), which comprise the CRIB motif and residues to its C-terminus, exhibit similar affinity for Cdc42 compared to the full-length kinase. The high-affinity e-CRIB fragments were then separated into two fragments, comprising the minimal CRIB motif (mCla4 and mSte20) and the C-terminal fragments (cCla4 and cSte20). In total, six target peptide sequences were chosen for expression and purification using the new expression system: eSte20, mSte20, cSte20, eCla4, mCla4 and cCla4 (FIG. 9). In FIG. 9, the "extended" CRIBs, eCla4 and eSte20 comprise 48 and 43 residues, respectively. The minimal CRIB fragments, mCla4 and mSte20, comprise 21 residues and contain the CRIB consensus sequence (highlighted). The C-terminal CRIB fragments (cCla4 and cSte20) are derived from the sequence segments to the C-terminus of the consensus CRIB motif.

The DNA fragments encoding the CRIB peptides from Cla4 and Ste20 were amplified from a cDNA library by PCR or synthesized as oligonucleotides using the codon preference of *E. coli*. The DNA fragments were digested with EcoR I and BamH I, and subcloned into the pTSN-6A vector (see Example 2, Osborne M., Su Z. & Ni F. et al., *J. Biomol. NMR*, 26; 317-326, 2003). The expression constructs were transformed into the DH5α host strain and the plasmid was purified with the Qiagen mini-prep kit. The construct was confirmed by DNA sequencing. A single methionine residue was inserted between the SFC120 fusion protein and the desired peptide sequence to facilitate release of the peptides from the fusion protein by CNBr cleavage. A His-tag with six histidines can be placed at the N-terminus of SFC120 to simplify purification of the fusion protein by adsorption onto a Ni-NTA agarose column (QIAGEN). In the present case, the His-tag SFC120 vector was used to express the eCRIB fragments (eSte20 and eCla4). The generic non-His-tag SFC120 was used to express the mCRIB and cCRIB fragments (mCla4, mSte20, cCla4, and cSte20).

Expression of the peptide fragments was achieved by transformation of the appropriate plasmid into *E. coli* BL21 (DE3) competent cells. An overnight culture grown in 2YT containing 100 μg/ml ampicillin (25 ml) was used to inoculate 1 L of M9 minimal media (100 μg/ml ampicillin) supplemented with BME vitamins solution (10 ml/L of 100× stock—SIGMA). $^{15}$N-labeled peptides (mCla4, mSte20, cCla4, cSte20, eSte20, eCla4) were expressed using $^{15}$(NH$_4$)$_2$SO$_4$ (2 g/L) as the sole nitrogen source. Uniformly $^{15}$N/$^{13}$C-labeled eSte20 was expressed using $^{15}$(NH$_4$)$_2$SO$_4$ (2 g/L) and $^{13}$C$_6$ glucose (2 g/L) as the sole nitrogen and carbon sources in the M9 media, respectively. The cells were grown at 37° C. to a cell density of OD$_{600}$=0.8 and induced by adding IPTG to a final concentration of 1 mM. The cells were incubated for 4-12 hours at 37° C. and collected by centrifugation (8,000 rpm for 20 min).

Expression of $^{15}$N-labeled eCla4

Figure 10:
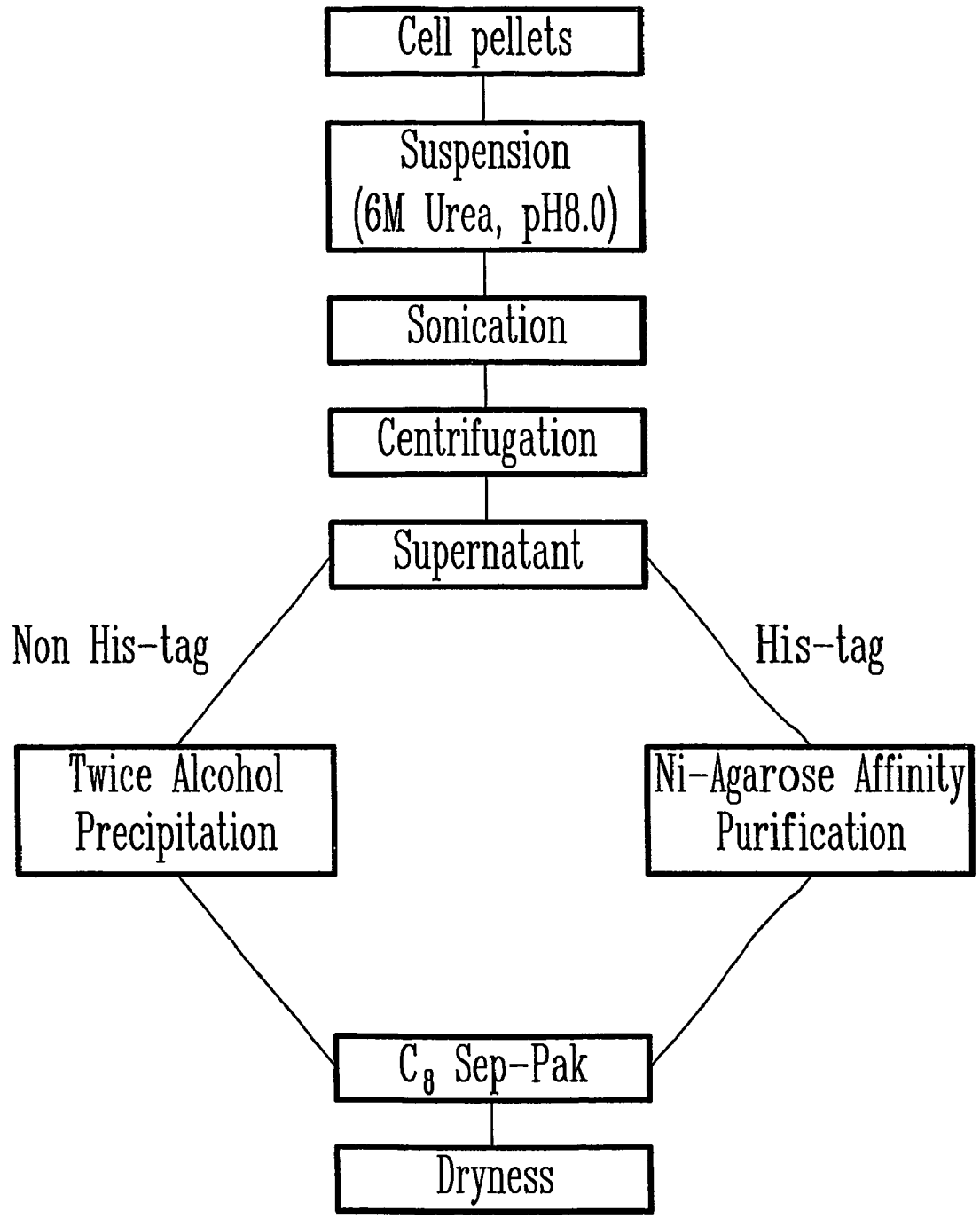
FIG. 10 illustrates a summary of the purification protocols for the SFC-fusion protein and the CRIB fragments.

A uniformly $^{15}$N enriched eCRIB peptide from Cla4 (FIG. 9) was obtained by growing the cells on minimal medium with ampicillin containing 1 g/L ($^{15}$NH$_4$)$_2$SO$_4$ and 5 g/L glucose as the sole sources of nitrogen and carbon. First a colony was picked from a LB plate and grown in 3 ml of LB for 5 hours. A 100 μl aliquot was transferred to 50 ml of minimal media and grown at 37° C. for overnight. This 50 ml solution was used to inoculate 1 L of the minimal media, which was then induced with 1 mM IPTG at OD$_{600}$=0.8 and harvested after 12-16 hours growth at 37° C. by centrifugation. A summary of the purification protocols for the peptides is shown in FIG. 10 and described in detail in the following sections.

Purification of non His-Tag Fusion Peptides: mCRIB and cCRIB Peptides

Figure 11A:
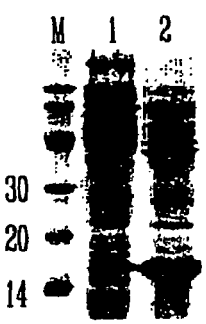
Figure 11B:
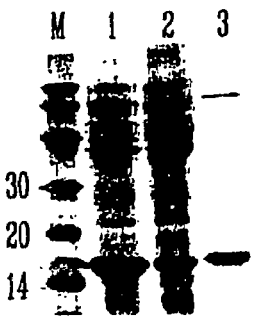
Figure 11C:
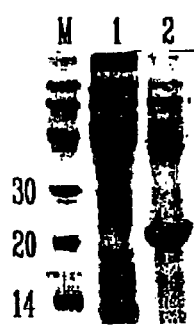
Figure 11D:

Thawed cell pellets were resuspended in 6 M urea in 20 mM Tris, 100 mM NaCl buffer, pH 8.0 for 4 hours and then sonicated for one minute on ice. The solution was then centrifuged at 7,000 rpm for 20 min. An equivolume of 100% cold ethanol was added to the supernatant and the solution allowed to stand at 4° C. for at least 2 hours. After centrifugation, the pellet containing precipitated DNA and large proteins was discarded and another equivolume of cold ethanol was added to the collected supernatant and allowed to stand overnight. The solution was centrifuged at 8,500 rpm and the pellet containing the relatively pure fusion-peptide fragment was subjected to SDS-PAGE analysis (FIGS. 11A to 11D). If necessary, the pellet was resuspended in 6 M urea and applied to a Sep-Pak™ column (Waters) to remove impurities. The fusion protein was then lyophilized. In FIG. 11A, lane M was loaded with molecular weight markers, lane 1 was loaded with uninduced cell lysate, and lane 2 was loaded with ITPG-induced cell lysate. In FIG. 11B, lane M was loaded with molecular weight marker, lane 1 was loaded with cell lysate, lane 2 was loaded with material from the pellet after the first alcohol precipitation; and lane 3 was loaded with material from the pellet after the second alcohol precipitation. In FIG. 11C, lane M was loaded with molecular weight markers, lane 1 was loaded with uninduced cell lysate and lane 2 was loaded with ITPG induced cell lysate. In FIG. 11D, lane M was loaded with molecular weight markers, lane 1 was loaded with flow through material, lanes 2 to 5 are loaded with wash fractions, and lane 6 was loaded with elution fraction.

Purification of His-Tag Fusion Peptides: eCRiBs

Cell pellets were resuspended in 6 M urea in Tris-HCl buffer at pH 8.0 by gentle shaking for ~4 h and briefly sonicated on ice. After centrifugation at 7,000 rpm for 20 min the supernatant was applied to a Ni-NTA agarose column (QIAGEN) previously equilibrated with the lysis buffer. The column was then washed with ~20 column volumes of 6 M urea in Tris buffer at pH 6.3 to eliminate non-specific binding to the column. The His-tagged fusion protein was then eluted with 6 M urea in 20 mM Tris buffer at pH 4.5. The solubilized fusion protein was then lyophilized to dryness after desalted with a Sep-Pak™ column (Waters). An aliquot from each step was taken to SDS-PAGE analysis (FIGS. 11A to 11D).

EXAMPLE 9

Expression of Thrombin Inhibition Peptide FD22

The FD22 peptide refers to an amino acid sequence of 22 residues which contains one thrombin substrate sequence linked to the HRC1 peptide by a native linking sequence of hirudin. FD22 has the amino acid sequence of Phe-Asp-Pro-Arg-Pro-Gln-Ser-His-Asn-Asp-Gly-Asp-Phe-Glu-Glu-Ile-Pro-Glu-Glu-Tyr-Leu-Gln (SEQ ID NO:39). The DNA sequence encoding the FD22 peptide was prepared by two synthetic oligonucleotides with two unique restriction enzyme sites of EcoR I and BamH I at two ends respectively.

Two complementary oligonucleotide primers were chemically synthesized and annealed in annealing buffer (see Example 4). The annealing mixture was cleaned up with the Qiagen PCR purification Kit. The insert (SEQ ID NO:40) was subcloned to the vector pMFH (see, Example 4). The expression construct pMFH-FD22 was transformed into the E coli DH5α strain and the plasmid was purified with the Qiagen mini-prep kit. The identity of the insert was confirmed by DNA sequencing. A single methionine residue was inserted between the MFH fusion carrier protein and the FD22 peptide sequence to facilitate release of the peptide by CNBr cleavage.

Expression of the MFH-FD22 fusion protein was achieved by transformation of the plasmid into E. coli BL21(DE3) competent cells. An overnight culture grown in LB containing 100 μg/ml ampicillin (50 ml) was used to inoculate 1 L of LB medium supplemented with 100 μg/ml ampicillin. $^{15}$N-labeled FD22 peptides were expressed using $^{15}(NH_4)_2SO_4$ (1 g/L) as the sole nitrogen source in M9 medium. The cells were grown at 37° C. to a cell density of $OD_{600}$=0.8 and induced by adding IPTG to a final concentration of 2 mM. The cells were incubated for 12 hours at 37° C. and collected by centrifugation (8000 rpm for 20 min). The cell pellet was frozen at −20° C. for future use.

Figure 12:
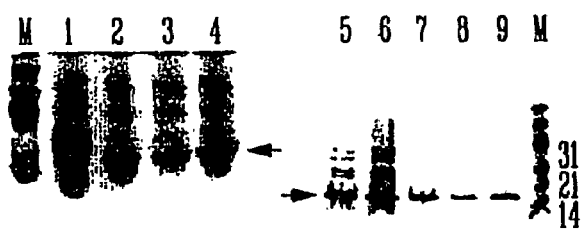
FIG. 12 illustrates a SDS-PAGE of expressed SFC-FD22 fusion protein.

Thawed cell pellets were resuspended in 6 M urea in 20 mM Tris, 100 mM NaCl buffer, pH 8.0 for 4 hours and then sonicated for one minute on ice. The solution was then centrifuged at 7,000 rpm for 20 min. The supernatant was subjected to the purification by Ni-NTA affinity chromatography under a denaturing condition (see the purification part in Example 8). The eluate containing MFH-FD22 was applied to a Sep-Pak™ column (Waters) to remove salts. The purified fusion protein was then lyophilized. An aliquot from each step was taken to SDS-PAGE analysis (FIG. 12). In FIG. 12, lane M was loaded with molecular weight markers, lane 1 was loaded with uninduced cell lysate, lanes 2 to 4 were loaded with ITPG induced cell lysate, lanes 5 and 6 were loaded with cell lysate, lane 7 was loaded with Ni-NTA beads with bound fusion protein, and lanes 8 to 9 were loaded with material from the elution.

EXAMPLE 10

Expression of Ephrin B Peptides (EB2 and EB3)

Eph receptors are a unique family of receptor tyrosine kinases and play critical roles in cell development and adulthood, in regulating cell migration and in defining compartments. Their plasma-membrane-bound ligands, ephrins, are thought to orchestrate cell movements by transducing bidirectional tyrosine-kinase-mediated signals into both cells expressing the receptors and cells expressing the ligands. To transduce reverse signals, the B-class cell-attached ephrins mediate contact-dependent cell-cell communications and transduce the contact signals to the host cells through the association of their cytoplasmic domains with other cytoplasmic proteins (Willinson D., Nat. Rev. Neurosci., 2; 155-164, 2001).

The EB2 or EB3 peptide refers to the cytoplasmic carboxyl-terminal 33 amino acid residue sequence which are conserved among ephrin B1, ephrin B2 and ephrin B3. This particular peptide is responsible for binding to downstream partners such as Grb4 and RGS3 proteins. The amino acid sequence of EB2 or EB3 peptide is Cys-Pro-His-Tyr-Glu-Lys-Val-Ser-Gly-Asp-Tyr-Gly-His-Pro-Val-Tyr-Ile-Val-Gln-Glu/ (Asp)-Met/(Gly)-Pro-Pro-Gln-Ser-Pro-Ala/(Pro)-Asn-Ile-Tyr-Lys-Val (SEQ ID NO:41). The DNA sequences encoding the EB2 or EB3 peptides were amplified by two synthetic oligonucleotides with two unique restriction enzyme sites of EcoR I and BamH I at two ends, respectively (SEQ ID NO:42 and SEQ ID NO:43). In order to avoid truncation by cyanogen bromide, an acidic cleavage site of Asp-Pro (or Gly-Pro) sequence was inserted in the N-terminal of EB2 peptide. Two oligonucleotide primers are overlapped with 18 base pairs.

The PCR reaction was performed with a standard PCR procedure in one Perkin-Elmer PCR amplifier. The PCR fragment was digested with EcoR I and BamH I, and purified with the Qiagen PCR purification Kit. The insert was subcloned to the vector pMFH (see, Example 4). The expression construct pMFH-EB2 was transformed into the E coli DH5α strain and the plasmid was purified with Qiagen mini-prep kit. The identity of the insert was confirmed by DNA sequencing. An Asp-Pro residue linker was inserted between the MFH carrier protein and the EB2 peptide sequence to facilitate release of the peptides by formic acid.

Expression of the MFH-EB2 fusion protein was achieved by transformation of the plasmid into E. coli BL21 (DE3) competent cells. An overnight culture grown in 2YT containing 100 μg/ml ampicillin (50 ml) was used to inoculate 1 L of LB medium supplemented with 100 μg/ml ampicillin. $^{15}$N-labeled EB2 peptides was expressed using $^{15}(NH_4)_2SO_4$ (1 g/L) as the sole nitrogen source in M9 medium. The cells were grown at 37° C. to a cell density of $OD_{600}$=0.8 and induced by adding IPTG to a final concentration of 2 mM. The cells were incubated for 12 h at 37° C. and collected by centrifugation (8000 rpm for 20 min). The cell pellet was frozen at −20° C. for future use.

Figure 13:
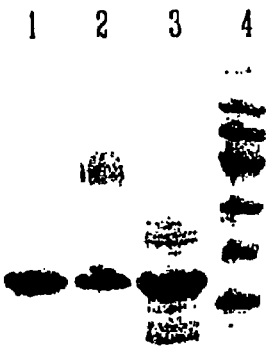
FIG. 13 illustrates a SDS-PAGE of expressed MFH-EB fusion proteins.

Thawed cell pellets were resuspended in 6 M urea in 20 mM Tris, 100 mM NaCl buffer, pH 8.0 for 4 hours and then sonicated for one minute on ice. The solution was then centrifuged at 7,000 rpm for 20 min. The supernatant was subjected to the purification by Ni-NTA affinity chromatography under a denaturing condition (see the purification part in Example 8). The eluate containing MFH-EB2 was applied to a Sep-Pak™ column (Waters) to remove salts. The purified fusion protein was then lyophilized. An aliquot from each step was taken to SDS-PAGE analysis (FIG. 13). In FIG. 13, lanes 1 and 2 were loaded with material from the expression of MFH-EB2 induced with IPTG, lane 3 was loaded with material from expression of MFH-EB3 induced with IPTG and lane 4 was loaded with molecular weight marker.

EXAMPLE 11

Expression of Propeptide of Human Cathepsin B, PRO

Cathepsin B is synthesized as a latent precursor, which is subsequently converted into the mature single- and two-chain forms by autoprocessing to remove its propeptide (Mach, L.

et al., *Biochem. J.,* 293; 437-442, 1993; and Mach, L. et al., *J. Biol. Chem.,* 269; 13030-13035, 1994). Propeptide of cathepsin B (PRO) contains 62 amino acid residues and is the shortest one in the family. A number of studies have indicated that peptides derived from the proregion of various protease zymogens can inhibit their corresponding enzymes. The propeptide of rat cathepsin B, for example, is a potent inhibitor of the mature enzyme with high selectivity with $K_i$=0.4 nM at pH 6.0 (Fox, T. et al., *Biochemistry,* 31; 12571-12576, 1992).

The cDNA of the human cathepsin B propeptide (see FIG. 14) was amplified by PCR with Pfu polymerase. The PCR products were digested with BamH I and EcoR I, and purified by Qiagen PCR purification Kit. The fragment was subcloned into pHSN vector with standard procedure. The sequence of the resulting construct of pHSN-PRO was confirmed by DNA sequencing.

The construct was transformed into *E. coli* strain BL21 (DE3) to over-express the fusion protein. The cells were grown in LB supplemented with 50 μg/ml of amplicin overnight and used as a 0.1% inoculum for 1 liter. The cells were grown at 37° C. to late exponential phase (OD600 nm≈0.8) and induced with 1 mM isopropyl-β-thiogalactosidose (IPTG) for at least four hours. Production of $^{15}$N-labelled HSN-PRO fusion protein in the pHSN -PRO/BL21 system was performed in M9 minimal medium using $^{15}$N—(NH$_4$)$_2$SO$_4$ as the sole nitrogen source. When the OD$_{600\ nm}$ reached 0.8, the induction was initiated by adding 1 mM IPTG. After a further at least four-hour culture, the cells were harvested.

The harvested cells were re-suspended in denaturing Buffer A (50 mM phosphate, pH 8.0, 5 mM Tris, 50 mM NaCl, 6M urea). The suspension was lysated for 3 hours on ice. After clarification, the HSN-PRO fusion protein was purified with Ni-NTA affinity agarose from Qiagen. The fusion protein was eluted with Buffer A in the presence of 200 mM Imidazole.

The fusion protein was refolded by dialysis against a large bulk of Buffer A in the absence of urea for overnight. The solution was clarified by centrifugation and concentrated with CentriPrep™.

Figure 16A:
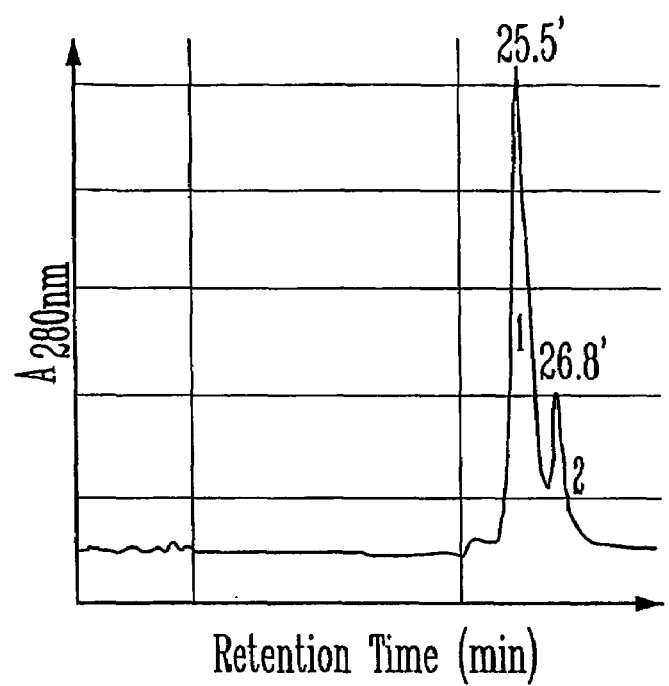
FIGS. 16A and 16B illustrate the purification of the PRO peptide (produced in the fusion protein of FIG. 15B) by HPLC (FIG. 16A) and analysis by mass spectroscopy (FIG. 16B)
Figure 16B:
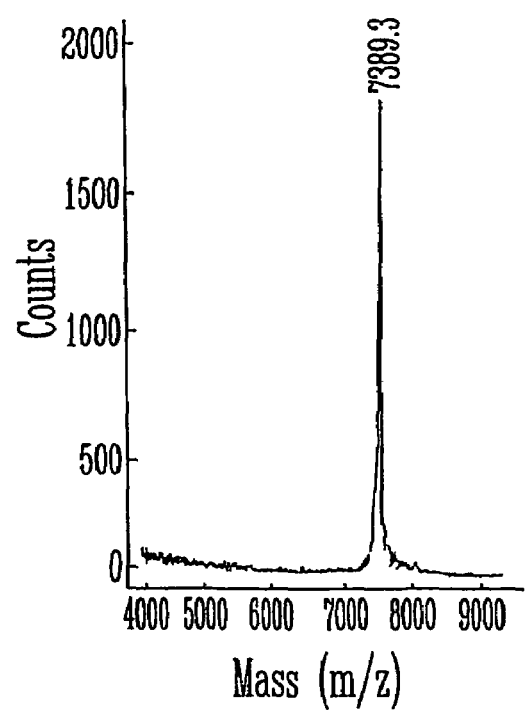

To release the propeptide, the HSN-PRO fusion protein was cleaved by thrombin for 30 minutes to two hours at room temperature. An aliquot from the reaction mixture was taken in every 15 minutes to evaluate the cleavage process by 20% SDS-PAGE PHAST™ gel (FIG. 15). For bulk purification, the reaction was terminated by urea-denaturation. The undigested fusion protein and the carrier protein were removed by Ni-NTA Agarose as described above. The flow-through was subjected to HPLC purification with a reverse-phase HPLC chromatographic C$_{18}$ Vydax™ semi-preparative column with a flow rate of 5 ml/min. The column was equilibrated with 0.1% TFA in water until a stable baseline was attained. Sample was subsequently loaded onto the column. The products were eluted with a gradient of acetonitrile from 0 to 50% over 30 min (FIG. 16). The identity of the purified PRO was confirmed by mass spectroscopy (FIG. 16) and lyophilized and kept at −20° C.

Figure 17:
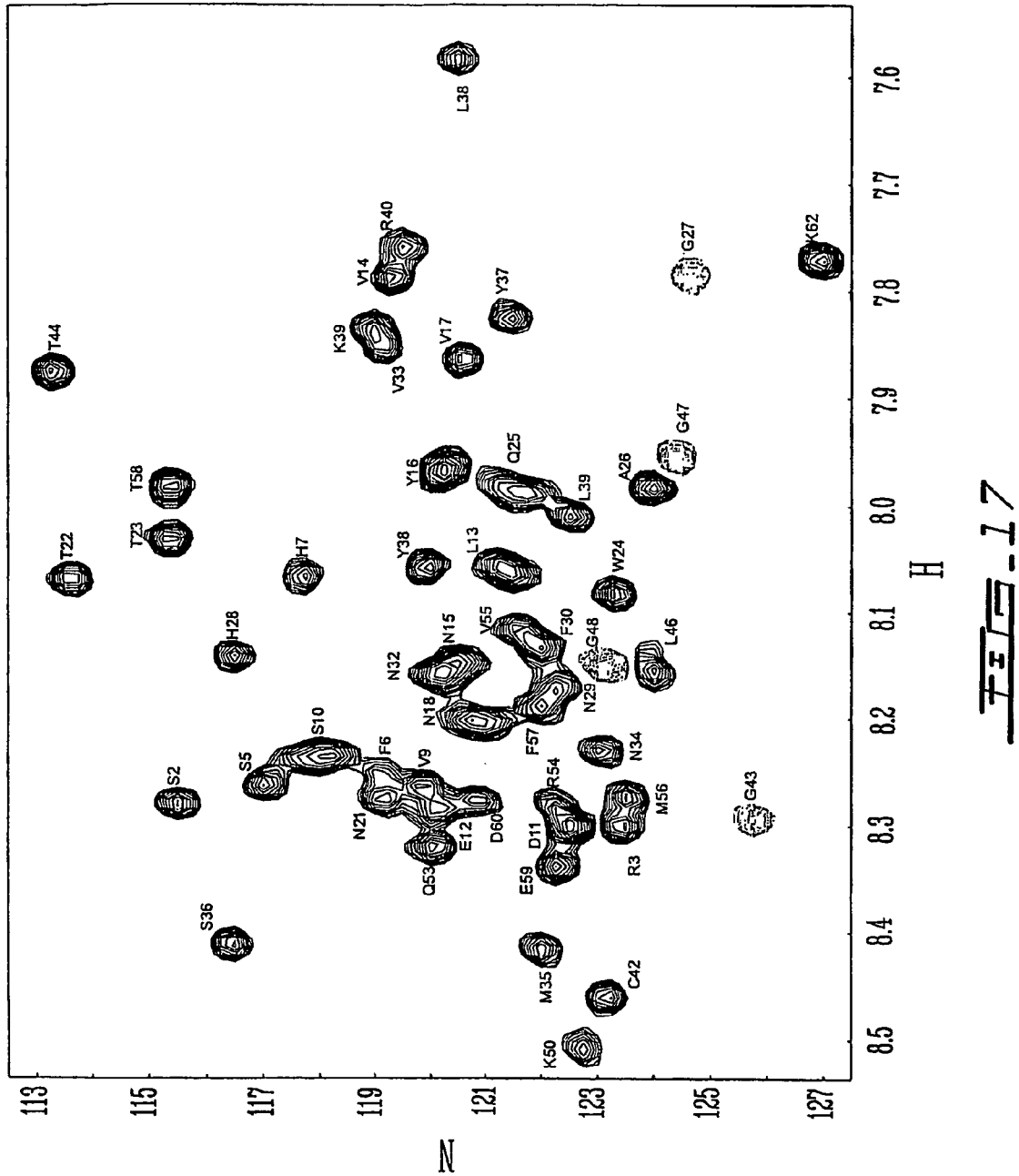
FIG. 17 illustrates $^1$H-$^{15}$N HSQC spectra of the PRO peptide with assignments.

$^1$H-$^{15}$N heteronuclear single-quantum correlation (HSQC) spectra were acquired at 500 or 800 MHz using a standard pulse sequence (Mori, S. et al., *J. Magn. Reson. B,* 108; 94-98, 1995). 3D experiments including HSQC, HSQC-NOESY and HSQC-TOCSY were carried out with 800 MHz. Spectral processing, display and analysis were performed using the XwinNMR software package supplied with the spectrometer system. Sequence specific assignment of the propeptide HSQC spectrum was carried out with NMRview 4.0 (Johnson, B. et al., *J. Biomol. NMR.,* 4; 603-614, 1994). The $^1$H-$^{15}$N HSQC spectrum of PRO is shown in FIG. 17.

EXAMPLE 12

CNBr Cleavage of SFC-CRIBs and Purification of the CRIB Peptides

CNBr cleavage was used to release the target peptide from the fusion protein. The fusion protein was dissolved in 70% TFA and CNBr added to a final molar ratio of 100:1 and the solution allowed to stand for ~24 h. The samples were then diluted with water (×10) and lyophilized to dryness and purified by RP-HPLC on a C18 column using an acetonitrile-water gradient containing 0.1% TFA. The peptides were lyophilized and confirmed by electrospray mass spectrometry.

Typical yields of the purified peptides chosen for expression described herein were very high, ranging from 30-40 mg/L in LB medium. Significantly, high quantities of pure peptides were also obtained from growths in M9 minimal media (15-20 mg/L in M9 media grown in H$_2$O) facilitating uniform isotopic enrichment of the peptides with $^{13}$C and $^{15}$N for NMR studies. Indeed, it was found herein that enough peptide for NMR studies could be isolated from only 0.5 L of M9 minimal media, making this expression system attractive as an alternative to other systems requiring more expensive isotope labeled media. Moreover high yields, up to 12 mg/L, are obtained for growth in M9 with 99.9% D$_2$O. Previous workers have reported expression of CRIB fragments of similar length to the eCRIB's reported here (Abdul-Manan N. et al., *Nature,* 399; 379-383, 1999; Mott H. et al, *Nature,* 399; 384-388, 1999; Morreale, A., et al., *Nat. Struct. Biol.,* 7; 384-388, 2000; and Gizachew, D. et al., *Biochemistry,* 39; 3963-3971, 2000). In those studies, GST was used as a fusion carrier, however, expression was significantly lower than reported here, requiring special minimal media (BIOexpress (CIL) or Celtone (Martek)) for enrichment.

Figure 18:
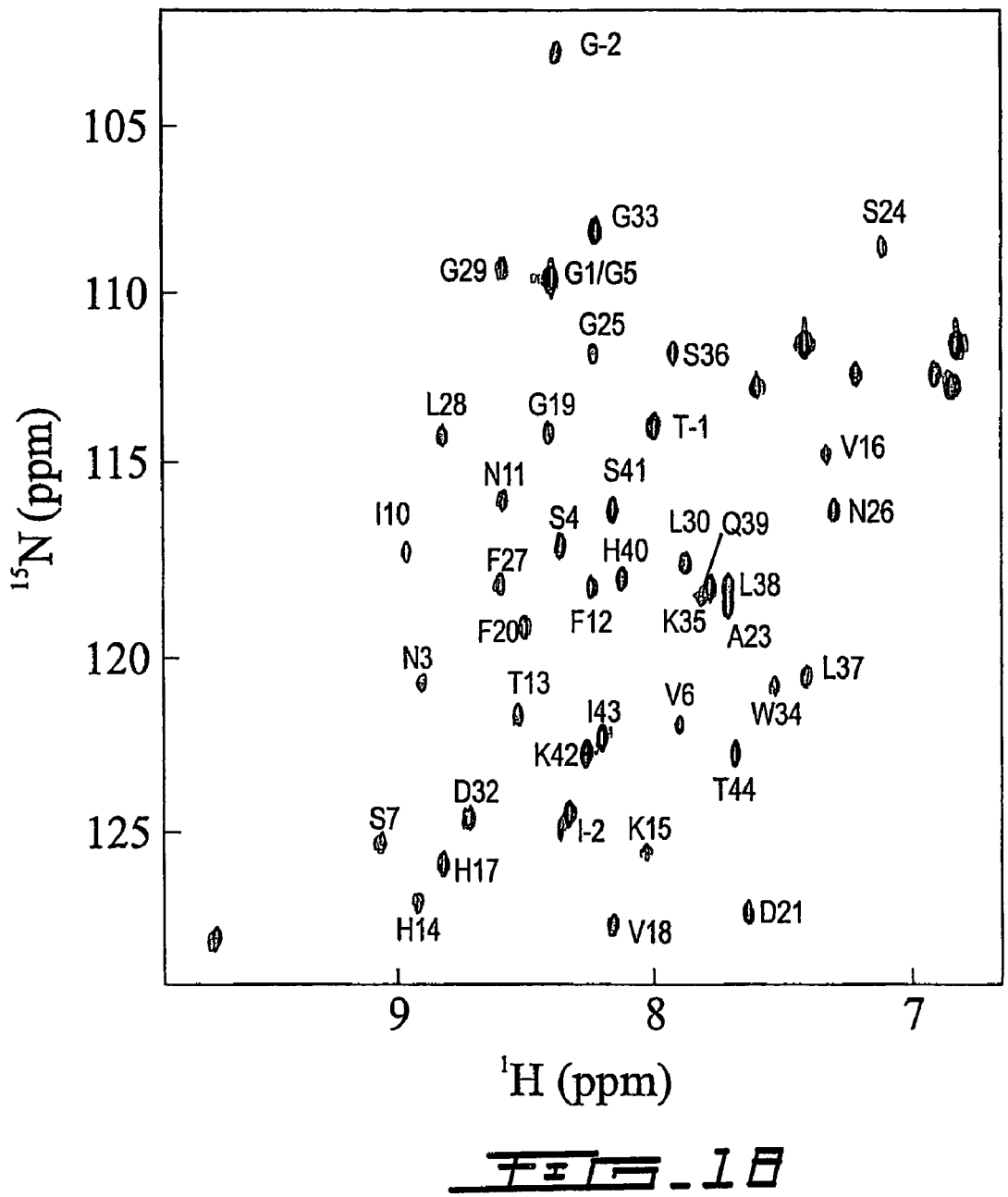
FIG. 18 illustrates $^1$H-$^{15}$N HSQC spectra of $^{15}$N-eCla4 fragment in complex with unlabelled Cdc42.

The $^1$H-$^{15}$N HSQC spectrum for one of the eCRIB fragments is shown in FIG. 18. FIG. 18 shows the $^{15}$N-$^1$H HSQC spectrum of $^{15}$N-eCla4 in complex with unlabeled Cdc42.

The data on the yields of the fusion proteins and CRIB peptides are listed in Table 2.

EXAMPLE 13

Cleavage of the MFH-FD22 Fusion Protein and Purification of the FD22 Peptide

Figure 19:
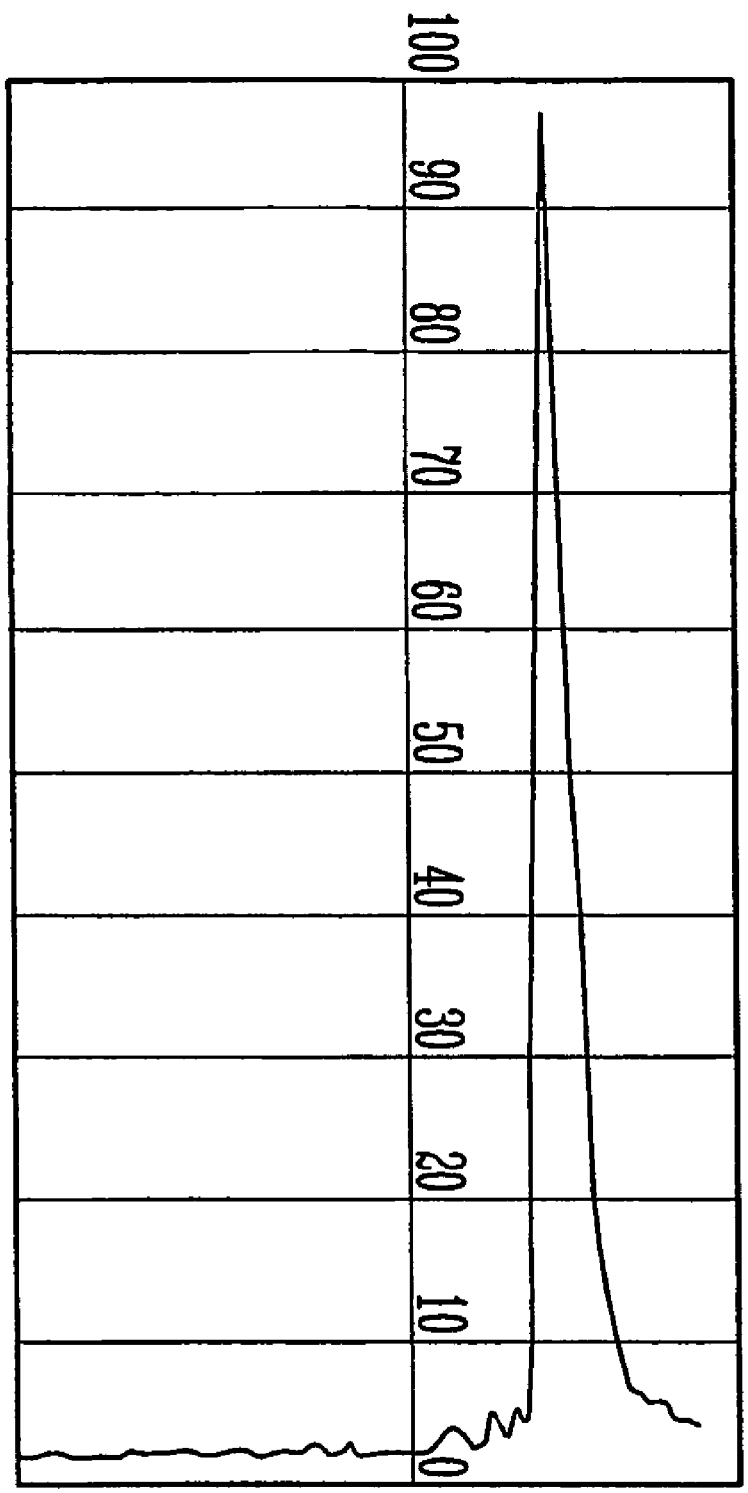
FIG. 19 illustrates the HPLC profile of FD22 after the carrier protein was removed with CNBr cleavage and Ni-NTA affinity chromatography.

CNBr cleavage was used to release the target peptide from the fusion protein. The fusion protein was dissolved in 0.1 M HCl and 6 M guanidine hydrochloride (10 mg protein/ml). Crystal CNBr was added to a final molar ratio of 100:1 of the fusion protein. The solution was allowed to stand for 12~24 hours. The samples were then purified with Ni-NTA beads to remove the MFH carrier protein and undigested MFH-FD22 fusion protein. The flow-through was further purified by RP-HPLC on a C$_{18}$ column using an acetonitrile-water gradient containing 0.1% TFA (FIG. 19). The peptides were lyophilized and confirmed by electrospray mass spectrometry. In FIG. 19, a reversed phase semi-preparative column (C$_{18}$) was used and the sample was eluted with a concentration gradient of acetonitrile from 10% to 70% and with a flow rate of 5 ml/min. The retention time of FD22 peptide is around 12 min. The wavelength of the detector was set at 278 nm.

Figure 20:
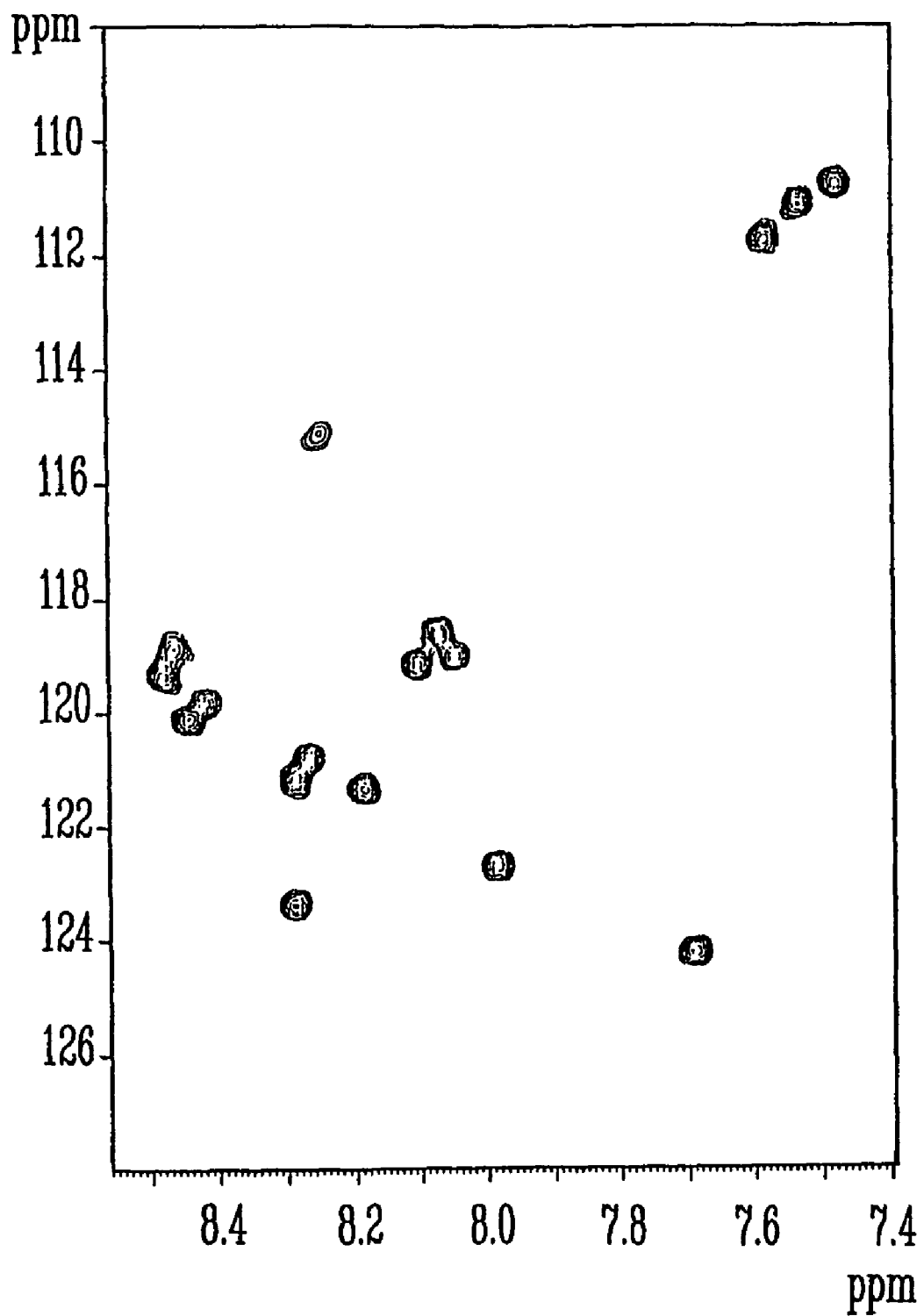
FIG. 20 illustrates $^1$H-$^{15}$N HSQC spectra of the FD22 peptide.

$^1$H-$^{15}$N heteronuclear single-quantum correlation (HSQC) spectra were acquired at 500 or 800 MHz using a standard pulse sequence (Mori, S. et al., *J. Magn. Reson. B,* 108; 94-98, 1995). 3D experiments including HSQC, HSQC-NOESY and HSQC-TOCSY were carried out with 800 MHz. Spectral processing, display and analysis were performed using the XwinNMR software package supplied with the spectrometer system. Sequence specific assignment of peptide HSQC spectrum was done with NMRview 4.0 (Johnson, B. et al., *J. Biomol. NMR*, 4; 603-614, 1994). The $^1$H-$^{15}$N HSQC spectrum of FD22 is shown in FIG. 20.

The data on the yields of the fusion proteins and purified peptides are listed in Table 2.

EXAMPLE 14

Figure 21:
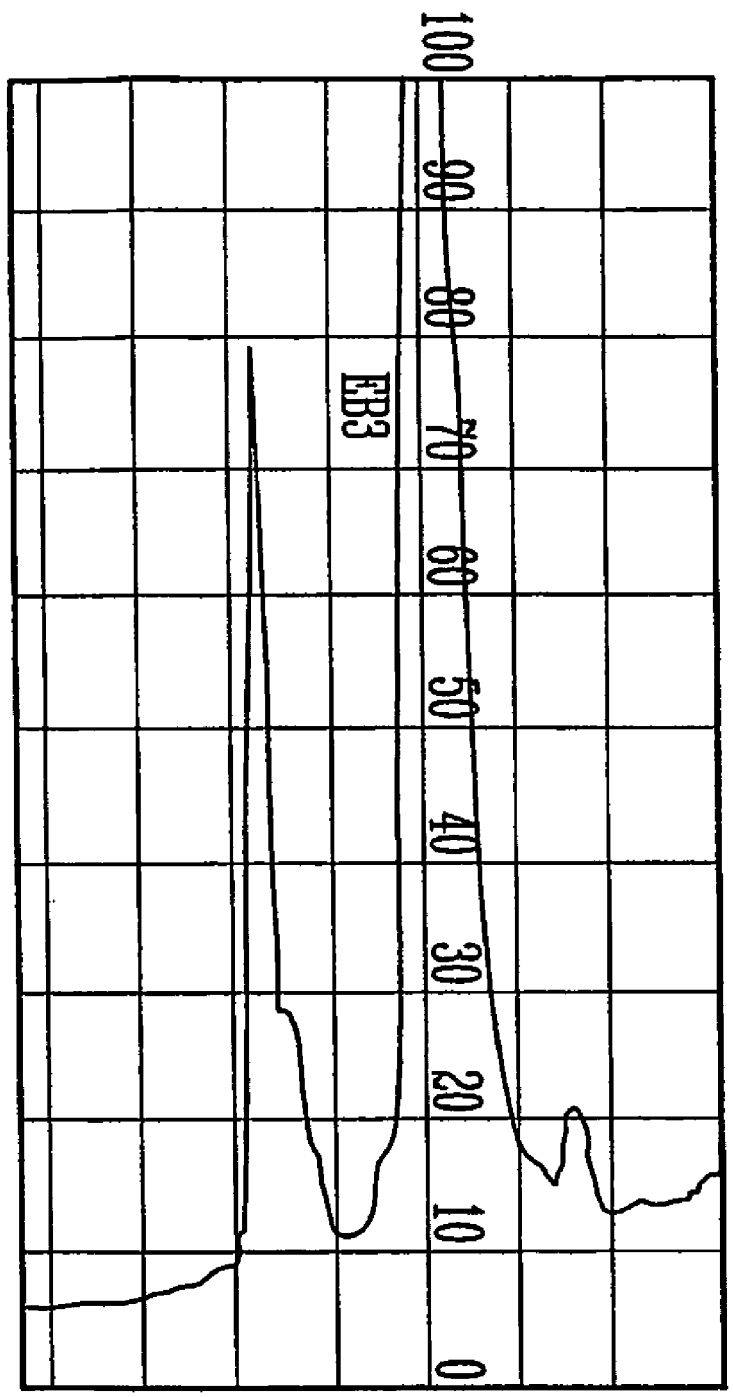
FIG. 21 illustrates the HPLC profile of the EB3 peptide after the carrier protein was removed by CNBr cleavage and Ni-NTA affinity chromatography.

Cleavage of the Fusion Protein of MFH-EB2 and Purification of the EB2 Peptide Acid cleavage was used to release the target peptide from the fusion protein. The fusion protein was dissolved in 50% formic acid and the protein concentration is 10 mg protein/ml. The solution was allowed to stand for 12~24 hours in dark. The samples were then diluted with water (×100) and lyophilized to dryness. The Ni-NTA affinity chromatography was used to remove the MHF carrier protein and undigested MFH-EB2 fusion protein. The flow-through containing the EB2 peptide was purified by RP-HPLC on a C18 column using an acetonitrile-water gradient containing 0.1% TFA (FIG. 21). The peptides were lyophilized and confirmed by electrospray mass spectrometry. In FIG. 21, a reversed phase semi-preparative column ($C_{18}$) was used and the sample was eluted with a concentration gradient of acetonitrile from 10% to 70% and with a flow rate of 5 ml/min. The retention time of the EB2 peptide is around 18 min. The wavelength of the detector was set at 278 nm.

$^1$H-$^{15}$N heteronuclear single-quantum correlation (HSQC) spectra were acquired at 500 or 800 MHz using a standard pulse sequence (Mori, S. et al., *J. Magn. Reson. B*, 108; 94-98, 1995). 3D experiments including HSQC, HSQC-NOESY and HSQC-TOCSY were carried out with 800 MHz. Spectral processing, display and analysis were performed using the XwinNMR software package supplied with the spectrometer system. Sequence specific assignment of peptide HSQC spectrum was carried out with NMRview 4.0 (Johnson, B. et al., *J. Biomol. NMR*, 4; 603-614, 1994). The $^1$H-$^{15}$N HSQC spectrum of EB2 is shown in FIG. 22.

The data on the yields of the fusion protein and EB2 peptide are listed in Table 2.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. An isolated and/or purified nucleic acid sequence encoding a fusion protein comprising at least one target peptide linked to a fusion carrier protein, the fusion carrier protein consisting of an amino acid sequence as set forth in SEQ ID NO: 14.

2. An expression vector comprising the nucleic acid sequence of claim 1, operably linked to a promoter for expression of said nucleic acid sequence coding for the fusion protein.

3. The expression vector of claim 2, wherein the promoter is pL promoter, λ promoter, trc promoter or T7 promoter.

4. A host cell transformed with the expression vector of claim 2.

5. The host cell of claim 4, wherein said host cell is *E. coli* DH5α, BL21, JM101 or JM105 or NM522 or N99CI+.

6. The host cell of claim 4, wherein said host cell is from *E. coli* or *B. subtilis*.

7. The host cell of claim 4, wherein said host cell is a yeast.

8. A method for producing a fusion protein comprising the step of culturing the host cell as defined in claim 4 under suitable conditions for expression of the expression vector, thereby producing a fusion protein.

9. The method of claim 8, wherein the host cell is induced by an inducer to express the expression vector.

10. The method of claim 9, wherein the inducer is IPTG, nalidixic acid or a temperature suitable for inducing expression of the vector.

11. The method of claim 8, further comprising a step of purification of the fusion protein produced.

12. The method of claim 11, wherein the step of purification comprises at least one of alcohol precipitation, ion-exchange, and affinity purification using Ni-agarose resin.

13. The method of claim 8, wherein the fusion protein is further subjected to a proteolytic digestion to release the target peptide from the fusion protein.

14. The method of claim 13, wherein the proteolytic digestion is achieved by CNBr, formic acid or HCl.

15. The method of claim 13, wherein the proteolytic digestion is achieved by thrombin, or a protease.

16. The method of claim 15, wherein the protease is an enterokinase.

17. The method of claim 13, wherein the target peptide released is further purified by HPLC.

18. The nucleic acid sequence of claim 1, wherein the at least one target peptide is selected from the group consisting of eCla4, eCla5, hirudin, mCla4, mSte20, cCla4, cSte20, FpA, FN22, propeptide of human Cathepsin B, PTH and EphrinB, or fragments thereof.

19. The nucleic acid sequence of claim 1, wherein the fusion protein comprises a peptidic cleavage site between the at least one target peptide and the fusion carder protein.

* * * * *

SEQUENCE LISTING

<160> NUMBER OF SEQ ID NOS: 48

<210> SEQ ID NO 1
<211> LENGTH: 25
<212> TYPE: PRT
<213> ORGANISM: Staphylococcus nuclease

<400> SEQUENCE: 1

Ala Thr Ser Thr Lys Lys Leu His Lys Glu Pro Ala Thr Leu Ile Lys
1               5                   10                  15

Ala Ile Asp Gly Asp Thr Val Lys Leu
            20                  25

<210> SEQ ID NO 2
<211> LENGTH: 5
<212> TYPE: PRT
<213> ORGANISM: Staphylococcus nuclease

<400> SEQUENCE: 2

Tyr Lys Gly Gln Pro
1               5

<210> SEQ ID NO 3
<211> LENGTH: 29
<212> TYPE: PRT
<213> ORGANISM: Staphylococcus nuclease

<400> SEQUENCE: 3

Leu Leu Leu Val Asp Thr Pro Glu Thr Lys His Pro Lys Lys Gly Val
1               5                   10                  15

Glu Lys Tyr Gly Pro Glu Ala Ser Ala Phe Thr Lys Lys
            20                  25

<210> SEQ ID NO 4

```
<211> LENGTH: 32
<212> TYPE: PRT
<213> ORGANISM: Staphylococcus nuclease

<400> SEQUENCE: 4

Val Glu Asn Ala Lys Lys Ile Glu Val Glu Phe Asp Lys Gly Gln Arg
 1               5                  10                  15

Thr Asp Lys Tyr Gly Arg Gly Leu Ala Tyr Ile Tyr Ala Asp Gly Lys
            20                  25                  30

<210> SEQ ID NO 5
<211> LENGTH: 5
<212> TYPE: PRT
<213> ORGANISM: Staphylococcus nuclease

<400> SEQUENCE: 5

Val Asn Glu Ala Leu
 1               5

<210> SEQ ID NO 6
<211> LENGTH: 6
<212> TYPE: PRT
<213> ORGANISM: Staphylococcus nuclease

<400> SEQUENCE: 6

Phe Asn Pro Arg Gly Ser
 1               5

<210> SEQ ID NO 7
<211> LENGTH: 14
<212> TYPE: PRT
<213> ORGANISM: Staphylococcus nuclease

<400> SEQUENCE: 7

Val Arg Gln Gly Leu Ala Lys Val Ala Tyr Val Tyr Lys Pro
 1               5                  10

<210> SEQ ID NO 8
<211> LENGTH: 32
<212> TYPE: PRT
<213> ORGANISM: Staphylococcus nuclease

<400> SEQUENCE: 8

Asn Asn Thr His Glu Gln Leu Leu Arg Lys Ser Glu Ala Gln Ala Lys
 1               5                  10                  15

Lys Glu Lys Leu Asn Ile Trp Ser Glu Asp Asn Ala Asp Ser Gly Gln
            20                  25                  30

<210> SEQ ID NO 9
<211> LENGTH: 4
<212> TYPE: PRT
<213> ORGANISM: Artificial Sequence
<220> FEATURE:
<223> OTHER INFORMATION: Peptidic Cleavage Site found on the fusion
      carrier protein derived from Staphylococcus nuclease

<400> SEQUENCE: 9

Phe Asn Pro Arg
 1

<210> SEQ ID NO 10
<211> LENGTH: 4
<212> TYPE: PRT
<213> ORGANISM: Artificial Sequence
<220> FEATURE:
```

<223> OTHER INFORMATION: Peptidic Cleavage Site found on the fusion
      carrier protein derived from Staphylococcus nuclease

<400> SEQUENCE: 10

Leu Val Pro Arg
 1

<210> SEQ ID NO 11

<400> SEQUENCE: 11

000

<210> SEQ ID NO 12
<211> LENGTH: 5
<212> TYPE: PRT
<213> ORGANISM: Artificial Sequence
<220> FEATURE:
<223> OTHER INFORMATION: Peptidic Cleavage Site found on the fusion
      carrier protein derived from Staphylococcus nuclease

<400> SEQUENCE: 12

Asp Asp Asp Asp Lys
 1               5

<210> SEQ ID NO 13
<211> LENGTH: 351
<212> TYPE: DNA
<213> ORGANISM: Artificial Sequence
<220> FEATURE:
<223> OTHER INFORMATION: Fusion Carrier Protein named SFC120
<220> FEATURE:
<221> NAME/KEY: CDS
<222> LOCATION: (1)...(351)

<400> SEQUENCE: 13

```
gca act tca act aaa aaa tta cat aaa gaa cct gcg act tta att aaa      48
Ala Thr Ser Thr Lys Lys Leu His Lys Glu Pro Ala Thr Leu Ile Lys
 1               5                  10                  15 gcg att gat ggt gat acg gtt aaa tta atg tac aaa ggt caa cca atg      96
Ala Ile Asp Gly Asp Thr Val Lys Leu Met Tyr Lys Gly Gln Pro Met
                20                  25                  30 aca ttc aga cta tta ttg gtt gat aca cct gaa aca aag cat cct aaa     144
Thr Phe Arg Leu Leu Leu Val Asp Thr Pro Glu Thr Lys His Pro Lys
             35                  40                  45 aaa ggt gta gag aaa tat ggt cct gaa gca agt gca ttt acg aaa aaa     192
Lys Gly Val Glu Lys Tyr Gly Pro Glu Ala Ser Ala Phe Thr Lys Lys
     50                  55                  60 atg gta gaa aat gca aag aaa att gaa gtc gag ttt gac aaa ggt caa     240
Met Val Glu Asn Ala Lys Lys Ile Glu Val Glu Phe Asp Lys Gly Gln
 65                  70                  75                  80 aga act gat aaa tat gga cgt ggc tta gcg tat att tat gct gat gga     288
Arg Thr Asp Lys Tyr Gly Arg Gly Leu Ala Tyr Ile Tyr Ala Asp Gly
                 85                  90                  95 aaa atg gta aac gaa gct tta gtt cgt caa ggc ttg gct aaa gtt gct     336
Lys Met Val Asn Glu Ala Leu Val Arg Gln Gly Leu Ala Lys Val Ala
                100                 105                 110 tat gtt tac aaa cct                                                 351
Tyr Val Tyr Lys Pro
        115
```

<210> SEQ ID NO 14
<211> LENGTH: 117
<212> TYPE: PRT
<213> ORGANISM: Artificial Sequence

```
<220> FEATURE:
<223> OTHER INFORMATION: Fusion Carrier Protein named SFC120

<400> SEQUENCE: 14

Ala Thr Ser Thr Lys Lys Leu His Lys Glu Pro Ala Thr Leu Ile Lys
 1               5                  10                  15

Ala Ile Asp Gly Asp Thr Val Lys Leu Met Tyr Lys Gly Gln Pro Met
             20                  25                  30

Thr Phe Arg Leu Leu Leu Val Asp Thr Pro Glu Thr Lys His Pro Lys
         35                  40                  45

Lys Gly Val Glu Lys Tyr Gly Pro Glu Ala Ser Ala Phe Thr Lys Lys
     50                  55                  60

Met Val Glu Asn Ala Lys Lys Ile Glu Val Glu Phe Asp Lys Gly Gln
 65                  70                  75                  80

Arg Thr Asp Lys Tyr Gly Arg Gly Leu Ala Tyr Ile Tyr Ala Asp Gly
                 85                  90                  95

Lys Met Val Asn Glu Ala Leu Val Arg Gln Gly Leu Ala Lys Val Ala
            100                 105                 110

Tyr Val Tyr Lys Pro
            115

<210> SEQ ID NO 15
<211> LENGTH: 369
<212> TYPE: DNA
<213> ORGANISM: Artificial Sequence
<220> FEATURE:
<223> OTHER INFORMATION: Fusion Carrier Protein named SFC120 ( N118E,
      N119F)
<220> FEATURE:
<221> NAME/KEY: CDS
<222> LOCATION: (1)...(369)

<400> SEQUENCE: 15 aca gcc atg gca act tca act aaa aaa tta cat aaa gaa cct gcg act        48
Thr Ala Met Ala Thr Ser Thr Lys Lys Leu His Lys Glu Pro Ala Thr
 1               5                  10                  15 tta att aaa gcg att gat ggt gat acg gtt aaa tta atg tac aaa ggt        96
Leu Ile Lys Ala Ile Asp Gly Asp Thr Val Lys Leu Met Tyr Lys Gly
             20                  25                  30 caa cca atg aca ttc aga cta tta ttg gtt gat aca cct gaa aca aag      144
Gln Pro Met Thr Phe Arg Leu Leu Leu Val Asp Thr Pro Glu Thr Lys
         35                  40                  45 cat cct aaa aaa ggt gta gag aaa tat ggt cct gaa gca agt gca ttt      192
His Pro Lys Lys Gly Val Glu Lys Tyr Gly Pro Glu Ala Ser Ala Phe
     50                  55                  60 acg aaa aaa atg gta gaa aat gca aag aaa att gaa gtc gag ttt gac      240
Thr Lys Lys Met Val Glu Asn Ala Lys Lys Ile Glu Val Glu Phe Asp
 65                  70                  75                  80 aaa ggt caa aga act gat aaa tat gga cgt ggc tta gcg tat att tat      288
Lys Gly Gln Arg Thr Asp Lys Tyr Gly Arg Gly Leu Ala Tyr Ile Tyr
                 85                  90                  95 gct gat gga aaa atg gta aac gaa gct tta gtt cgt caa ggc ttg gct      336
Ala Asp Gly Lys Met Val Asn Glu Ala Leu Val Arg Gln Gly Leu Ala
            100                 105                 110 aaa gtt gct tat gtt tac aaa cct gaa ttc atg                          369
Lys Val Ala Tyr Val Tyr Lys Pro Glu Phe Met
            115                 120

<210> SEQ ID NO 16
<211> LENGTH: 123
<212> TYPE: PRT
```

<213> ORGANISM: Artificial Sequence
<220> FEATURE:
<223> OTHER INFORMATION: Fusion Carrier Protein named SFC120 ( N118E, N119F)

<400> SEQUENCE: 16

```
Thr Ala Met Ala Thr Ser Thr Lys Lys Leu His Lys Glu Pro Ala Thr
  1               5                  10                  15

Leu Ile Lys Ala Ile Asp Gly Asp Thr Val Lys Leu Met Tyr Lys Gly
             20                  25                  30

Gln Pro Met Thr Phe Arg Leu Leu Leu Val Asp Thr Pro Glu Thr Lys
         35                  40                  45

His Pro Lys Lys Gly Val Glu Lys Tyr Gly Pro Glu Ala Ser Ala Phe
     50                  55                  60

Thr Lys Lys Met Val Glu Asn Ala Lys Lys Ile Glu Val Glu Phe Asp
 65                  70                  75                  80

Lys Gly Gln Arg Thr Asp Lys Tyr Gly Arg Gly Leu Ala Tyr Ile Tyr
                 85                  90                  95

Ala Asp Gly Lys Met Val Asn Glu Ala Leu Val Arg Gln Gly Leu Ala
            100                 105                 110

Lys Val Ala Tyr Val Tyr Lys Pro Glu Phe Met
        115                 120
```

<210> SEQ ID NO 17
<211> LENGTH: 393
<212> TYPE: DNA
<213> ORGANISM: Artificial Sequence
<220> FEATURE:
<223> OTHER INFORMATION: bacterial expression vector pHSN-Met65Leu that encodes a fusion protein, containing a sequence for agene encoding the N-terminal nucleotide binding domain of staph. nuclease, designate
<220> FEATURE:
<221> NAME/KEY: CDS
<222> LOCATION: (1)...(393)

<400> SEQUENCE: 17

```
aca gcc atg gga cac cat cac cat cac cat ggc gca act tca act aaa      48
Thr Ala Met Gly His His His His His His Gly Ala Thr Ser Thr Lys
  1               5                  10                  15 aaa tta cat aaa gaa cct gcg act tta att aaa gcg att gat ggt gat      96
Lys Leu His Lys Glu Pro Ala Thr Leu Ile Lys Ala Ile Asp Gly Asp
             20                  25                  30 acg gtt aaa tta atg tac aaa ggt caa cca atg aca ttc aga cta tta    144
Thr Val Lys Leu Met Tyr Lys Gly Gln Pro Met Thr Phe Arg Leu Leu
         35                  40                  45 ttg gtt gat aca cct gaa aca aag cat cct aaa aaa ggt gta gag aaa    192
Leu Val Asp Thr Pro Glu Thr Lys His Pro Lys Lys Gly Val Glu Lys
     50                  55                  60 tat ggt cct gaa gca agt gca ttt acg aaa aaa ttg gta gaa aat gca    240
Tyr Gly Pro Glu Ala Ser Ala Phe Thr Lys Lys Leu Val Glu Asn Ala
 65                  70                  75                  80 aag aaa att gaa gtc gag ttt gac aaa ggt caa aga act gat aaa tat    288
Lys Lys Ile Glu Val Glu Phe Asp Lys Gly Gln Arg Thr Asp Lys Tyr
                 85                  90                  95 gga cgt ggc tta gcg tat att tat gct gat gga aaa atg gta aac gaa    336
Gly Arg Gly Leu Ala Tyr Ile Tyr Ala Asp Gly Lys Met Val Asn Glu
            100                 105                 110 gct tta gtt cgt caa ggc ttg gct aaa gtt gct tat gtt tac aaa cct    384
Ala Leu Val Arg Gln Gly Leu Ala Lys Val Ala Tyr Val Tyr Lys Pro
        115                 120                 125
```

```
gaa ttc atg                                                              393
Glu Phe Met
    130

<210> SEQ ID NO 18
<211> LENGTH: 131
<212> TYPE: PRT
<213> ORGANISM: Artificial Sequence
<220> FEATURE:
<223> OTHER INFORMATION: fusion protein encoded by bacterial expression
      vector pHSN-Met65Leu, containing a sequence for a gene encoding
      the N-terminal nucleotide binding domain of staph. nuclease,
      designated

<400> SEQUENCE: 18

Thr Ala Met Gly His His His His His His Gly Ala Thr Ser Thr Lys
1               5                   10                  15

Lys Leu His Lys Glu Pro Ala Thr Leu Ile Lys Ala Ile Asp Gly Asp
            20                  25                  30

Thr Val Lys Leu Met Tyr Lys Gly Gln Pro Met Thr Phe Arg Leu Leu
        35                  40                  45

Leu Val Asp Thr Pro Glu Thr Lys His Pro Lys Lys Gly Val Glu Lys
50                  55                  60

Tyr Gly Pro Glu Ala Ser Ala Phe Thr Lys Lys Leu Val Glu Asn Ala
65                  70                  75                  80

Lys Lys Ile Glu Val Glu Phe Asp Lys Gly Gln Arg Thr Asp Lys Tyr
                85                  90                  95

Gly Arg Gly Leu Ala Tyr Ile Tyr Ala Asp Gly Lys Met Val Asn Glu
            100                 105                 110

Ala Leu Val Arg Gln Gly Leu Ala Lys Val Ala Tyr Val Tyr Lys Pro
        115                 120                 125

Glu Phe Met
    130

<210> SEQ ID NO 19
<211> LENGTH: 369
<212> TYPE: DNA
<213> ORGANISM: Artificial Sequence
<220> FEATURE:
<223> OTHER INFORMATION: bacterial expression vector pMF that encodes a
      fusion protein, containing a sequence for a gene encoding the
      N-terminal nucleotide binding domain of staph. nuclease,
      designated SFC120
<220> FEATURE:
<221> NAME/KEY: CDS
<222> LOCATION: (1)...(369)

<400> SEQUENCE: 19 aca gcc atg gca act tca act aaa aaa tta cat aaa gaa cct gcg act     48
Thr Ala Met Ala Thr Ser Thr Lys Lys Leu His Lys Glu Pro Ala Thr
1               5                   10                  15 tta att aaa gcg att gat ggt gat acg gtt aaa tta ttg tac aaa ggt     96
Leu Ile Lys Ala Ile Asp Gly Asp Thr Val Lys Leu Leu Tyr Lys Gly
            20                  25                  30 caa cca ttg aca ttc aga cta tta ttg gtt gat aca cct gaa aca aag    144
Gln Pro Leu Thr Phe Arg Leu Leu Leu Val Asp Thr Pro Glu Thr Lys
        35                  40                  45 cat cct aaa aaa ggt gta gag aaa tat ggt cct gaa gca agt gca ttt    192
His Pro Lys Lys Gly Val Glu Lys Tyr Gly Pro Glu Ala Ser Ala Phe
50                  55                  60 acg aaa aaa ttg gta gaa aat gca aag aaa att gaa gtc gag ttt gac    240
Thr Lys Lys Leu Val Glu Asn Ala Lys Lys Ile Glu Val Glu Phe Asp
65                  70                  75                  80
```

```
aaa ggt caa aga act gat aaa tat gga cgt ggc tta gcg tat att tat      288
Lys Gly Gln Arg Thr Asp Lys Tyr Gly Arg Gly Leu Ala Tyr Ile Tyr
                85                  90                  95 gct gat gga aaa ttg gta aac gaa gct tta gtt cgt caa ggc ttg gct      336
Ala Asp Gly Lys Leu Val Asn Glu Ala Leu Val Arg Gln Gly Leu Ala
            100                 105                 110 aaa gtt gct tat gtt tac aaa cct gaa ttc atg                          369
Lys Val Ala Tyr Val Tyr Lys Pro Glu Phe Met
        115                 120
```

<210> SEQ ID NO 20
<211> LENGTH: 123
<212> TYPE: PRT
<213> ORGANISM: Artificial Sequence
<220> FEATURE:
<223> OTHER INFORMATION: fusion protein MF encoded by bacterial
      expression vector pMF, containing a sequence for a gene encoding
      the N-terminal nucleotide binding domain of staph. nuclease,
      designated

<400> SEQUENCE: 20

```
Thr Ala Met Ala Thr Ser Thr Lys Lys Leu His Lys Glu Pro Ala Thr
1               5                   10                  15

Leu Ile Lys Ala Ile Asp Gly Asp Thr Val Lys Leu Leu Tyr Lys Gly
            20                  25                  30

Gln Pro Leu Thr Phe Arg Leu Leu Leu Val Asp Thr Pro Glu Thr Lys
        35                  40                  45

His Pro Lys Lys Gly Val Glu Lys Tyr Gly Pro Glu Ala Ser Ala Phe
    50                  55                  60

Thr Lys Lys Leu Val Glu Asn Ala Lys Lys Ile Glu Val Glu Phe Asp
65                  70                  75                  80

Lys Gly Gln Arg Thr Asp Lys Tyr Gly Arg Gly Leu Ala Tyr Ile Tyr
                85                  90                  95

Ala Asp Gly Lys Leu Val Asn Glu Ala Leu Val Arg Gln Gly Leu Ala
            100                 105                 110

Lys Val Ala Tyr Val Tyr Lys Pro Glu Phe Met
        115                 120
```

<210> SEQ ID NO 21
<211> LENGTH: 390
<212> TYPE: DNA
<213> ORGANISM: Artificial Sequence
<220> FEATURE:
<223> OTHER INFORMATION: bacterial expression vector pMFH that encodes a
      fusion protein, containing a sequence for a gene encoding the
      N-terminal nucleotide binding domain of staph. nuclease,
      designated SFC1
<220> FEATURE:
<221> NAME/KEY: CDS
<222> LOCATION: (1)...(390)

<400> SEQUENCE: 21

```
aca gcc atg gca act tca act aaa aaa tta cat aaa gaa cct gcg act      48
Thr Ala Met Ala Thr Ser Thr Lys Lys Leu His Lys Glu Pro Ala Thr
1               5                   10                  15 tta att aaa gcg att gat ggt gat acg gtt aaa tta ttg tac aaa ggt      96
Leu Ile Lys Ala Ile Asp Gly Asp Thr Val Lys Leu Leu Tyr Lys Gly
            20                  25                  30 caa cca ttg aca ttc aga cta tta ttg gtt gat aca cct gaa aca aag     144
Gln Pro Leu Thr Phe Arg Leu Leu Leu Val Asp Thr Pro Glu Thr Lys
        35                  40                  45 cat cct aaa aaa ggt gta gag aaa tat ggt cct gaa gca agt gca ttt     192
```

```
His Pro Lys Lys Gly Val Glu Lys Tyr Gly Pro Glu Ala Ser Ala Phe
    50                  55                  60 acg aaa aaa ttg gta gaa aat gca aag aaa att gaa gtc gag ttt gac       240
Thr Lys Lys Leu Val Glu Asn Ala Lys Lys Ile Glu Val Glu Phe Asp
 65                  70                  75                  80 aaa ggt caa aga act gat aaa tat gga cgt ggc tta gcg tat att tat       288
Lys Gly Gln Arg Thr Asp Lys Tyr Gly Arg Gly Leu Ala Tyr Ile Tyr
                 85                  90                  95 gct gat gga aaa ttg gta aac gaa gct tta gtt cgt caa ggc ttg gct       336
Ala Asp Gly Lys Leu Val Asn Glu Ala Leu Val Arg Gln Gly Leu Ala
                100                 105                 110 aaa gtt gct tat gtt tac aaa cct cac cat cac cat cac cat atg gaa       384
Lys Val Ala Tyr Val Tyr Lys Pro His His His His His His Met Glu
                115                 120                 125 ttc atg                                                               390
Phe Met
    130
```

<210> SEQ ID NO 22
<211> LENGTH: 130
<212> TYPE: PRT
<213> ORGANISM: Artificial Sequence
<220> FEATURE:
<223> OTHER INFORMATION: fusion protein MFH encoded by bacterial
      expression vector pMFH, containing a sequence for a gene encoding
      the N-terminal nucleotide binding domain of staph. nuclease,
      designated

<400> SEQUENCE: 22

```
Thr Ala Met Ala Thr Ser Thr Lys Lys Leu His Lys Glu Pro Ala Thr
 1               5                  10                  15

Leu Ile Lys Ala Ile Asp Gly Asp Thr Val Lys Leu Leu Tyr Lys Gly
                20                  25                  30

Gln Pro Leu Thr Phe Arg Leu Leu Leu Val Asp Thr Pro Glu Thr Lys
                35                  40                  45

His Pro Lys Lys Gly Val Glu Lys Tyr Gly Pro Glu Ala Ser Ala Phe
    50                  55                  60

Thr Lys Lys Leu Val Glu Asn Ala Lys Lys Ile Glu Val Glu Phe Asp
 65                  70                  75                  80

Lys Gly Gln Arg Thr Asp Lys Tyr Gly Arg Gly Leu Ala Tyr Ile Tyr
                 85                  90                  95

Ala Asp Gly Lys Leu Val Asn Glu Ala Leu Val Arg Gln Gly Leu Ala
                100                 105                 110

Lys Val Ala Tyr Val Tyr Lys Pro His His His His His His Met Glu
                115                 120                 125

Phe Met
    130
```

<210> SEQ ID NO 23

<400> SEQUENCE: 23

000

<210> SEQ ID NO 24

<400> SEQUENCE: 24

000

<210> SEQ ID NO 25

```
<211> LENGTH: 48
<212> TYPE: DNA
<213> ORGANISM: Artificial Sequence
<220> FEATURE:
<223> OTHER INFORMATION: Forward oligonucleotide primer

<400> SEQUENCE: 25
catgccatgg gtttccacca tcaccatcac catgcaactt caactaaa                    48

<210> SEQ ID NO 26
<211> LENGTH: 54
<212> TYPE: DNA
<213> ORGANISM: Artificial Sequence
<220> FEATURE:
<223> OTHER INFORMATION: Reverse oligonucleotide primer

<400> SEQUENCE: 26
ggaagatctt tagaattccg cggatccacg cggctttaaat tgacctgaat cagc            54

<210> SEQ ID NO 27
<211> LENGTH: 11
<212> TYPE: PRT
<213> ORGANISM: Artificial Sequence
<220> FEATURE:
<223> OTHER INFORMATION: HCR1 peptide derived from the C-terminal 11
      amino acid residues of hirudin and strongly inhibiting thrombin

<400> SEQUENCE: 27

Asp Phe Glu Glu Ile Pro Glu Glu Tyr Leu Gln
 1               5                  10

<210> SEQ ID NO 28
<211> LENGTH: 48
<212> TYPE: DNA
<213> ORGANISM: Artificial Sequence
<220> FEATURE:
<223> OTHER INFORMATION: synthetic complementary oligonucleotide

<400> SEQUENCE: 28
aattcatggg tgacttcgaa gaaatcccgg aagaatacct gcagtaag                    48

<210> SEQ ID NO 29
<211> LENGTH: 48
<212> TYPE: DNA
<213> ORGANISM: Artificial Sequence
<220> FEATURE:
<223> OTHER INFORMATION: synthetic complementary oligonucleotide

<400> SEQUENCE: 29
gatccttact gcaggtattc ttccgggatt tcttcgaagt cacccatg                    48

<210> SEQ ID NO 30
<211> LENGTH: 4
<212> TYPE: PRT
<213> ORGANISM: Artificial Sequence
<220> FEATURE:
<223> OTHER INFORMATION: short peptide substrates for the thrombin
      active site

<400> SEQUENCE: 30

Leu Asp Pro Arg
 1

<210> SEQ ID NO 31
<211> LENGTH: 4
<212> TYPE: PRT
<213> ORGANISM: Artificial Sequence
```

```
<220> FEATURE:
<223> OTHER INFORMATION: short peptide substrates for the thrombin
      active site

<400> SEQUENCE: 31

Val Asp Pro Arg
 1

<210> SEQ ID NO 32
<211> LENGTH: 4
<212> TYPE: PRT
<213> ORGANISM: Artificial Sequence
<220> FEATURE:
<223> OTHER INFORMATION: short peptide substrates for the thrombin
      active site

<400> SEQUENCE: 32

Phe Asn Pro Arg
 1

<210> SEQ ID NO 33
<211> LENGTH: 4
<212> TYPE: PRT
<213> ORGANISM: Artificial Sequence
<220> FEATURE:
<223> OTHER INFORMATION: short peptide substrates for the thrombin
      active site

<400> SEQUENCE: 33

Pro Asn Pro Arg
 1

<210> SEQ ID NO 34
<211> LENGTH: 4
<212> TYPE: PRT
<213> ORGANISM: Artificial Sequence
<220> FEATURE:
<223> OTHER INFORMATION: short peptide substrates for the thrombin
      active site

<400> SEQUENCE: 34

Phe Ser Ala Arg
 1

<210> SEQ ID NO 35
<211> LENGTH: 4
<212> TYPE: PRT
<213> ORGANISM: Artificial Sequence
<220> FEATURE:
<223> OTHER INFORMATION: short peptide substrates for the thrombin
      active site

<400> SEQUENCE: 35

Val Ser Pro Arg
 1

<210> SEQ ID NO 36
<211> LENGTH: 36
<212> TYPE: PRT
<213> ORGANISM: Artificial Sequence
<220> FEATURE:
<223> OTHER INFORMATION: Recombinant Thrombin Target Peptide

<400> SEQUENCE: 36

Met Gly Leu Asp Pro Arg Met Gly Val Asp Pro Arg Met Gly Phe Asn
 1               5                  10                  15

Pro Arg Met Gly Pro Asn Pro Arg Met Gly Phe Ser Pro Arg Met Gly
```

```
                20                  25                  30
Val Ser Pro Arg
        35

<210> SEQ ID NO 37
<211> LENGTH: 63
<212> TYPE: DNA
<213> ORGANISM: Artificial Sequence
<220> FEATURE:
<223> OTHER INFORMATION: synthetic oligonucleotides

<400> SEQUENCE: 37
aattcatggg tctggatcct agaatgggag tagacccacg tatgggcttc aacccgcgca      60
tga                                                                    63

<210> SEQ ID NO 38
<211> LENGTH: 63
<212> TYPE: DNA
<213> ORGANISM: Artificial Sequence
<220> FEATURE:
<223> OTHER INFORMATION: synthetic oligonucleotides

<400> SEQUENCE: 38
gatctatggg tcctaaccca cgtatgggat ttagcgctcg catgggcgtt tctccacgtt      60
aat                                                                    63

<210> SEQ ID NO 39
<211> LENGTH: 22
<212> TYPE: PRT
<213> ORGANISM: Artificial Sequence
<220> FEATURE:
<223> OTHER INFORMATION: FD22 peptide refers to an amino acid sequence
      of 22 residues which contains one thrombin substrate sequence
      linked to the HRC1 peptide by a native linking sequence of hirudin

<400> SEQUENCE: 39

Phe Asp Pro Arg Pro Gln Ser His Asn Asp Gly Asp Phe Glu Glu Ile
 1               5                  10                  15

Pro Glu Glu Tyr Leu Gln
            20

<210> SEQ ID NO 40
<211> LENGTH: 78
<212> TYPE: DNA
<213> ORGANISM: Artificial Sequence
<220> FEATURE:
<223> OTHER INFORMATION: complementary oligonucleotide primer

<400> SEQUENCE: 40
aattcatgtt tgacccgcgc cctcaaagtc ataacgacgg tgattttgag gaaattcctg      60
aagagtattt acaataag                                                    78

<210> SEQ ID NO 41
<211> LENGTH: 33
<212> TYPE: PRT
<213> ORGANISM: Artificial Sequence
<220> FEATURE:
<223> OTHER INFORMATION: EB2 or EB3 peptide refers to cytoplasmic
      carboxyl-terminal 33 amino acid residue sequence which are
      conserved among ephrin B1, ephrin B2 and ephrin B3. This particular
      peptide is roteins
<220> FEATURE:
<221> NAME/KEY: VARIANT
<222> LOCATION: 20
<223> OTHER INFORMATION: Xaa = Glu or Asp
```

```
<220> FEATURE:
<221> NAME/KEY: VARIANT
<222> LOCATION: 21
<223> OTHER INFORMATION: Xaa = Met or Gly
<220> FEATURE:
<221> NAME/KEY: VARIANT
<222> LOCATION: 27
<223> OTHER INFORMATION: Xaa = Ala or Pro

<400> SEQUENCE: 41

Cys Pro His Tyr Glu Lys Val Ser Gly Asp Tyr Gly His Pro Val Tyr
 1               5                  10                  15

Ile Val Gln Xaa Xaa Pro Pro Gln Ser Pro Xaa Asn Ile Tyr Tyr Lys
            20                  25                  30

Val

<210> SEQ ID NO 42
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 42
ccggaattca tgtgcccgca ctacgaaaaa gtttccggtg actatggtca tccggtt        57

<210> SEQ ID NO 43
<211> LENGTH: 66
<212> TYPE: DNA
<213> ORGANISM: Artificial Sequence
<220> FEATURE:
<223> OTHER INFORMATION: synthetic oligonucleotide primer

<400> SEQUENCE: 43
cgcggatcct taaactttgt agtagatgtt tggcgggctc tgtggcggac catcctgaac     60
gatata                                                                66

<210> SEQ ID NO 44
<211> LENGTH: 48
<212> TYPE: PRT
<213> ORGANISM: Artificial Sequence
<220> FEATURE:
<223> OTHER INFORMATION: Candida Cla4 protein

<400> SEQUENCE: 44

Ser Val Leu Thr Gly Gly Asn Ser Gly Val Ser Gly Pro Ile Asn Phe
 1               5                  10                  15

Thr His Lys Val His Val Gly Phe Asp Pro Ala Ser Gly Asn Phe Thr
            20                  25                  30

Gly Leu Pro Asp Thr Trp Lys Ser Leu Leu Gln His Ser Lys Ile Thr
        35                  40                  45

<210> SEQ ID NO 45
<211> LENGTH: 44
<212> TYPE: PRT
<213> ORGANISM: Artificial Sequence
<220> FEATURE:
<221> NAME/KEY:
<222> LOCATION:
<223> OTHER INFORMATION: Candida Ste20 protein

<400> SEQUENCE: 45

Glu Val Asn Ile Lys Ile Ser Thr Pro Phe Asn Ala Lys His Leu Ala
 1               5                  10                  15
```

```
His Val Gly Ile Asp Xaa Asp Asn Gly Ser Tyr Thr Gly Leu Pro Ile
            20              25                  30

Glu Trp Glu Arg Leu Leu Ser Ala Ser Gly Ile Thr
        35                  40

<210> SEQ ID NO 46
<211> LENGTH: 186
<212> TYPE: DNA
<213> ORGANISM: Artificial Sequence
<220> FEATURE:
<223> OTHER INFORMATION: propeptide of human cathepsin B
<220> FEATURE:
<221> NAME/KEY: CDS
<222> LOCATION: (1)...(186)

<400> SEQUENCE: 46 cgg agc agg ccc tct ttc cat ccc gtg tcg gat gag ctg gtc aac tat      48
Arg Ser Arg Pro Ser Phe His Pro Val Ser Asp Glu Leu Val Asn Tyr
1               5                   10                  15 gtc aac aaa cgg aat acc acg tgg cag gcc ggg cac aac ttc tac aac      96
Val Asn Lys Arg Asn Thr Thr Trp Gln Ala Gly His Asn Phe Tyr Asn
            20                  25                  30 gtg gac atg agc tac ttg aag agg cta tgt ggt acc ttc ctg ggt ggg     144
Val Asp Met Ser Tyr Leu Lys Arg Leu Cys Gly Thr Phe Leu Gly Gly
        35                  40                  45 ccc aag cca ccc cag aga gtt atg ttt acc gag gac ctg aag             186
Pro Lys Pro Pro Gln Arg Val Met Phe Thr Glu Asp Leu Lys
    50                  55                  60

<210> SEQ ID NO 47
<211> LENGTH: 62
<212> TYPE: PRT
<213> ORGANISM: Artificial Sequence
<220> FEATURE:
<223> OTHER INFORMATION: propeptide of human cathepsin B

<400> SEQUENCE: 47

Arg Ser Arg Pro Ser Phe His Pro Val Ser Asp Glu Leu Val Asn Tyr
1               5                   10                  15

Val Asn Lys Arg Asn Thr Thr Trp Gln Ala Gly His Asn Phe Tyr Asn
            20                  25                  30

Val Asp Met Ser Tyr Leu Lys Arg Leu Cys Gly Thr Phe Leu Gly Gly
        35                  40                  45

Pro Lys Pro Pro Gln Arg Val Met Phe Thr Glu Asp Leu Lys
    50                  55                  60

<210> SEQ ID NO 48
<211> LENGTH: 14
<212> TYPE: PRT
<213> ORGANISM: Artificial Sequence
<220> FEATURE:
<223> OTHER INFORMATION: CRIB concensus which comprise the CRIB motif
<220> FEATURE:
<221> NAME/KEY: VARIANT
<222> LOCATION: (1)...(14)
<223> OTHER INFORMATION: Xaa = any amino acid

<400> SEQUENCE: 48

Ile Ser Xaa Pro Xaa Xaa Phe Xaa His Xaa Xaa His Val Gly
1               5                   10
```